(12) United States Patent
Morgan et al.

(10) Patent No.: US 7,595,322 B2
(45) Date of Patent: Sep. 29, 2009

(54) HETEROCYCLIC SULFONAMIDES AS MODULATORS OF CARDIAC SARCOMERES

(75) Inventors: Bradley Paul Morgan, Moraga, CA (US); Fady Malik, Burlingame, CA (US); Erica Anne Kraynack, Belmont, CA (US); Alexander Ramon Muci, San Francisco, CA (US); Xiangping Qian, Foster City, CA (US); David J. Morgans, Jr., Los Altos, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 358 days.

(21) Appl. No.: 10/550,398

(22) PCT Filed: Mar. 26, 2004

(86) PCT No.: PCT/US2004/009408

§ 371 (c)(1),
(2), (4) Date: Sep. 20, 2006

(87) PCT Pub. No.: WO2004/086865

PCT Pub. Date: Oct. 14, 2004

(65) Prior Publication Data

US 2007/0078126 A1    Apr. 5, 2007

Related U.S. Application Data

(60) Provisional application No. 60/458,702, filed on Mar. 27, 2003.

(51) Int. Cl.
    A61K 31/496       (2006.01)
(52) U.S. Cl. .................. 514/255.05; 544/360; 544/369; 544/370
(58) Field of Classification Search .................. 544/360, 544/369, 370
    See application file for complete search history.

(56) References Cited

U.S. PATENT DOCUMENTS

| 3,055,905 | A | 9/1962 | Graf et al. |
| 3,567,746 | A | 3/1971 | Shetty |
| 6,207,829 | B1 * | 3/2001 | Dunn et al. .................. 544/262 |

FOREIGN PATENT DOCUMENTS

| DE | 19912638 A1 | 9/2000 |
| DE | 19929076 A1 | 12/2000 |
| EP | 0107735 A | 5/1984 |
| EP | 0994115 A | 4/2000 |
| GB | 882090 A | 11/1961 |
| WO | WO 00/26202 A | 5/2000 |
| WO | WO 2004/018414 A | 3/2004 |

OTHER PUBLICATIONS

West, Anthony R., Solid State Chemistry and its Applications, Wiley, New York, 1988, pp. 358 and 365.*
European Supplementary Search Report for European Application No. EP04758456.0, completed Mar. 25, 2008.
Asakawa et al., "*Chemistry of Salicylic Acid and Anthranllic Acid. IV. Synthesis of 6-Chloro-5-sulfamoyl- and 6-Chloro-3-sulfamoylanthranllic Acid Derivatives,*" Chemical and Pharmaceutical Bulletin, Pharmaceutical Society of Japan, Tokyo, JP, 27(6):2187-2198 (1979).
El-Sharief et al., "*Synthesis of Different Types of Chlorinated Sulfonamides with Expected Insecticidal and Bactericidal Activities,*" Proceedings of the Indian National Science Academy, Part A, Physical Sciences, Indian National Science Academy, New Delhi, IN, 53(1):179-188 (1987).
Jucker et al., "*Konstitution und salldiuretischer Effekt von 3-Sulfamyl-4-chlorbenzoesäure-Derivaten und verwandten Verbindungen,*" Arzneimittel Forschung, Drug Research, ECV Editio Cantor Verlag, Aulendorf, DE, 13(4):269-280 (1963).
Pinto De Souza et al., "*Synthesis of 3-methyl-1(2H)-isoquinolinone Derivatives and Their Biological Activities,*" Indian Journal of Chemistry, Section B: Organic and Medicinal Chemistry, Scientific Publishers, Jodhpur, IN, 29B(10):961-965 (1990).
Künzle et al., "70. Dibenz[b,f]-1,4-oxazepin-11(10H)-one und Dibenz[b,e]-1,4-oxazepin -11(5H)-one," Helvetica Chimica Acta, vol. 52, Fasc. 3, No. 70, pp. 622-628 (1969).
International Search Report and Written Opinion mailed Sep. 9, 2004, for International Application No. PCT/US2004/09408, filed Mar. 26, 2004.

* cited by examiner

*Primary Examiner*—James O Wilson
*Assistant Examiner*—Brian McDowell
(74) *Attorney, Agent, or Firm*—Finnegan, Henderson, Farabow, Garrett & Dunner, LLP

(57) ABSTRACT

Certain substituted sulfonamide derivatives of Formula I selectively modulate the cardiac sarcomere, for example by potentiating cardiac myosin, and are useful in the treatment of systolic heart failure including congestive heart failure.

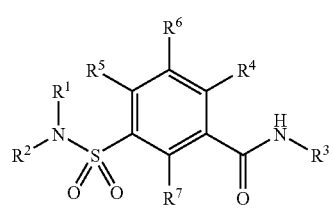

Formula I

10 Claims, No Drawings

HETEROCYCLIC SULFONAMIDES AS MODULATORS OF CARDIAC SARCOMERES

CROSS-REFERENCE TO RELATED APPLICATIONS

This application claims the benefit of co-pending provisional U.S. Applications Ser. No. 60/458,702, filed Mar. 27, 2003; which is incorporated herein by reference.

FIELD OF THE INVENTION

The invention relates to substituted sulfonamide derivatives, particularly to compounds that selectively modulate the cardiac sarcomere, and specifically to compounds, pharmaceutical formulations and methods of treatment for systolic heart failure, including congestive heart failure.

BACKGROUND OF THE INVENTION

The Cardiac Sarcomere

The "sarcomere" is an elegantly organized cellular structure found in cardiac and skeletal muscle made up of interdigitating thin and thick filaments; it comprises nearly 60% of cardiac cell volume. The thick filaments are composed of "myosin," the protein responsible for transducing chemical energy (ATP hydrolysis) into force and directed movement. Myosin and its functionally related cousins are called motor proteins. The thin filaments are composed of a complex of proteins. One of these proteins, "actin" (a filamentous polymer) is the substrate upon which myosin pulls during force generation. Bound to actin are a set of regulatory proteins, the "troponin complex" and "tropomyosin," which make the actin-myosin interaction dependent on changes in intracellular $Ca^{2+}$ levels. With each heartbeat, $Ca^{2+}$ levels rise and fall, initiating cardiac muscle contraction and then cardiac muscle relaxation (Robbins J and Leinwand L A. (1999) *Molecular Basis of Cardiovascular Disease*, Chapter 8. editor Chien, K. R., W.B. Saunders, Philadelphia). Each of the components of the sarcomere contributes to its contractile response.

Myosin is the most extensively studied of all the motor proteins. Of the thirteen distinct classes of myosin in human cells, the myosin-II class is responsible for contraction of skeletal, cardiac, and smooth muscle. This class of myosin is significantly different in amino acid composition and in overall structure from myosin in the other twelve distinct classes (Goodson H V and Spudich J A. (1993) Proc. Natl. Acad. Sci. USA 90:659-663). Myosin-II consists of two globular head domains linked together by a long alpha-helical coiled-coiled tail that assembles with other myosin-IIs to form the core of the sarcomere's thick filament. The globular heads have a catalytic domain where the actin binding and ATP functions of myosin take place. Once bound to an actin filament, the release of phosphate (cf. ATP to ADP) leads to a change in structural conformation of the catalytic domain that in turn alters the orientation of the light-chain binding lever arm domain that extends from the globular head; this movement is termed the powerstroke. This change in orientation of the myosin head in relationship to actin causes the thick filament of which it is a part to move with respect to the thin actin filament to which it is bound (Spudich J A. (2001) Nat Rev Mol Cell Biol. 2(5):387-92). Un-binding of the globular head from the actin filament (also $Ca^{2+}$ modulated) coupled with return of the catalytic domain and light chain to their starting conformation/orientation completes the contraction and relaxation cycle.

Mammalian heart muscle consists of two forms of cardiac myosin, alpha and beta, and they are well characterized (Robbins, supra). The beta form is the predominant form (>90 percent) in adult human cardiac muscle. Both have been observed to be regulated in human heart failure conditions at both transcriptional and translational levels (Miyata supra), with the alpha form being down-regulated in heart failure.

The sequences of all of the human skeletal, cardiac, and smooth muscle myosins have been determined. While the cardiac alpha and beta myosins are very similar (93% identity), they are both considerably different from human smooth muscle (42% identity) and more closely related to skeletal myosins (80% identity). Conveniently, cardiac muscle myosins are incredibly conserved across mammalian species. For example, both alpha and beta cardiac myosins are >96% conserved between humans and rats, and the available 250-residue sequence of porcine cardiac beta myosin is 100% conserved with the corresponding human cardiac beta myosin sequence. Such sequence conservation contributes to the predictability of studying myosin based therapeutics in animal based models of heart failure.

The components of the cardiac sarcomere present targets for the treatment of heart failure, for example by increasing contractility or facilitating complete relaxation to modulate systolic and diastolic function, respectively.

Heart Failure

Congestive heart failure ("CHF") is not a specific disease, but rather a constellation of signs and symptoms, all of which are caused by an inability of the heart to adequately respond to exertion by increasing cardiac output. The dominant pathophysiology associated with CHF is systolic dysfunction, an impairment of cardiac contractility (with a consequent reduction in the amount of blood ejected with each heartbeat). Systolic dysfunction with compensatory dilation of the ventricular cavities results in the most common form of heart failure, "dilated cardiomyopathy," which is often considered to be one in the same as CHF. The counterpoint to systolic dysfunction is diastolic dysfunction, an impairment of the ability to fill the ventricles with blood, which can also result in heart failure even with preserved left ventricular function. Congestive heart failure is ultimately associated with improper function of the cardiac myocyte itself, involving a decrease in its ability to contract and relax.

Many of the same underlying conditions can give rise to systolic and/or diastolic dysfunction, such as atherosclerosis, hypertension, viral infection, valvular dysfunction, and genetic disorders. Patients with these conditions typically present with the same classical symptoms: shortness of breath, edema and overwhelming fatigue. In approximately half of the patients with dilated cardiomyopathy, the cause of their heart dysfunction is ischemic heart disease due to coronary atherosclerosis. These patients have had either a single myocardial infarction or multiple myocardial infarctions; here, the consequent scarring and remodeling results in the development of a dilated and hypocontractile heart. At times the causative agent cannot be identified, so the disease is referred to as "idiopathic dilated cardiomyopathy." Irrespective of ischemic or other origin, patients with dilated cardiomyopathy share an abysmal prognosis, excessive morbidity and high mortality.

The prevalence of CHF has grown to epidemic proportions as the population ages and as cardiologists have become more successful at reducing mortality from ischemic heart disease, the most common prelude to CHF. Roughly 4.6 million people in the United States have been diagnosed with CHF; the incidence of such diagnosis is approaching 10 per 1000 after 65 years of age. Hospitalization for CHF is usually the result of inadequate outpatient therapy. Hospital discharges for CHF rose from 377,000 (in 1979) to 957,000 (in 1997) making CHF the most common discharge diagnosis in people age 65 and over. The five-year mortality from CHF approaches 50% (Levy D. (2002) New Engl J. Med. 347(18): 1442-4). Hence, while therapies for heart disease have greatly improved and life expectancies have extended over the last several years, new and better therapies continue to be sought, particularly for CHF.

"Acute" congestive heart failure (also known as acute "decompensated" heart failure) involves a precipitous drop in heart function resulting from a variety of causes. For example in a patient who already has congestive heart failure, a new myocardial infarction, discontinuation of medications, and dietary indiscretions may all lead to accumulation of edema fluid and metabolic insufficiency even in the resting state. A therapeutic agent that increases heart function during such an acute episode could assist in relieving this metabolic insufficiency and speeding the removal of edema, facilitating the return to the more stable "compensated" congestive heart failure state. Patients with very advanced congestive heart failure particularly those at the end stage of the disease also could benefit from a therapeutic agent that increases heart function, for example, for stabilization while waiting for a heart transplant. Other potential benefits could be provided to patients coming off a bypass pump, for example, by administration of an agent that assists the stopped or slowed heart in resuming normal function. Patients who have diastolic dysfunction (insufficient relaxation of the heart muscle) could benefit from a therapeutic agent that modulates relaxation.

Therapeutic Active Agents

Inotropes are drugs that increase the contractile ability of the heart. As a group, all current inotropes have failed to meet the gold standard for heart failure therapy, i.e., to prolong patient survival. In addition, current agents are poorly selective for cardiac tissue, in part leading to recognized adverse effects that limit their use. Despite this fact, intravenous inotropes continue to be widely used in acute heart failure (e.g., to allow for reinstitution of oral medications or to bridge patients to heart transplantation) whereas in chronic heart failure, orally given digoxin is used as an inotrope to relieve patient symptoms, improve the quality of life, and reduce hospital admissions.

Given the limitations of current agents, new approaches are needed to improve cardiac function in congestive heart failure. The most recently approved short-term intravenous agent, milrinone, is now nearly fifteen years old. The only available oral drug, digoxin, is over 200 hundred years old. There remains a great need for agents that exploit new mechanisms of action and may have better outcomes in terms of relief of symptoms, safety, and patient mortality, both short-term and long-term. New agents with an improved therapeutic index over current agents will provide a means to achieve these clinical outcomes.

The selectivity of agents directed at the cardiac sarcomere (for example, by targeting cardiac beta myosin) has been identified as an important means to achieve this improved therapeutic index. The present invention provides such agents (particularly sarcomere activating agents) and methods for their identification and use.

SUMMARY OF THE INVENTION

The present invention provides compounds, pharmaceutical compositions and methods for the treatment of heart failure including CHF, particularly systolic heart failure. The compositions are selective modulators of the cardiac sarcomere, for example, potentiating cardiac myosin.

In one aspect, the invention relates to one or more compounds of the group represented by Formula I:

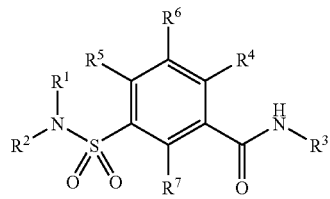

Formula I wherein:
$R^1$ and $R^2$ are independently selected from the group consisting of hydrogen, optionally substituted alkyl, optionally substituted aryl, optionally substituted heteroaryl, optionally substituted aralkyl, and optionally substituted heteroaralkyl; or $R^1$, $R^2$ and the nitrogen to which they are attached form an optionally substituted 5-, 6-, or 7-membered heterocyclic ring;

$R^3$ is an optionally substituted aryl or optionally substituted heteroaryl;

$R^4$ is halogen;

$R^5$ is hydrogen, halogen, hydroxy, or optionally substituted lower alkyl; and $R^6$ and $R^7$ are independently selected from the group consisting of hydrogen, halogen, hydroxy, and optionally substituted lower alkyl;

including single stereoisomers, mixtures of stereoisomers, and the pharmaceutically acceptable salts, solvates, and solvates of pharmaceutically acceptable salts thereof. The compounds of Formula I are useful as active agents in practice of the methods of treatment and in manufacture of the pharmaceutical formulations of the invention, and as intermediates in the synthesis of such active agents.

Yet other aspects of the invention relate to a pharmaceutical formulation including a pharmaceutically acceptable excipient, and to a method of treatment for heart disease, each entailing a therapeutically effective amount of a compound, isomer, salt or solvate represented by Formula I.

In an additional aspect, the present invention provides methods of screening for compounds that will bind to myosin (particularly myosin II or β myosin), for example compounds that will displace or compete with the binding of the compounds of Formula I. The methods comprise combining an optionally-labeled compound of Formula I, myosin, and at least one candidate agent and determining the binding of the candidate agent to myosin.

In a further aspect, the invention provides methods of screening for modulators of the activity of myosin. The methods comprise combining a compound of Formula I, myosin, and at least one candidate agent and determining the effect of the candidate agent on the activity of myosin.

Other aspects and embodiments will be apparent to those skilled in the art form the following detailed description.

DETAILED DESCRIPTION

The present invention provides compounds useful in selective modulation of the cardiac sarcomere, for example, by potentiating cardiac myosin. The compounds can be used to treat heart failure including CHF, particularly systolic heart failure. The invention further relates to pharmaceutical formulations comprising compounds of the invention, and to methods of treatment employing such compounds or compositions. The compositions are selective modulators of the cardiac sarcomere, for example, potentiating cardiac myosin.

Definitions

As used in the present specification, the following words and phrases are generally intended to have the meanings as set forth below, except to the extent that the context in which they are used indicates otherwise. The following abbreviations and terms have the indicated meanings throughout:

Ac=acetyl
Boc=t-butyloxy carbonyl
c-=cyclo
CBZ=carbobenzoxy=benzyloxycarbonyl
DCM=dichloromethane=methylene chloride=$CH_2Cl_2$
DIEA=DIPEA=N,N-diisopropylethylamine
DMF=N,N-dimethylformamide
DMSO=dimethyl sulfoxide
Et=ethyl
EtOAc=ethyl acetate
EtOH=ethanol
GC=gas chromatograghy
h=hour
HATU=O-(7-azabenzotriazol-1-yl)-N,N,N',N'-tetramethyluronium hexafluorophosphate
HBTU=2-(1H-benzotriazole-1-yl)-1,1,3,3-tetramethyluronium hexafluorophosphate
HOAt=7-aza-1-hydroxybenzotriazole
HOBt=1-Hydroxybenzotriazole
Me=methyl
min=minute
mL=milliliter
Ph=phenyl
rt=room temperature
s-=secondary
t-=tertiary
TES=triethylsilane
TFA=trifluoroacetic acid
THF=tetrahydrofuran
TLC=thin layer chromatography The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined below. It will be understood by those skilled in the art with respect to any group containing one or more substituents that such groups are not intended to introduce any substitution or substitution patterns that are sterically impractical, synthetically non-feasible and/or inherently unstable.

"Alkyl" is intended to include linear, branched, or cyclic hydrocarbon structures and combinations thereof. Lower alkyl refers to alkyl groups of from 1 to 5 carbon atoms. Examples of lower alkyl groups include methyl, ethyl, propyl, isopropyl, butyl, s-and t-butyl and the like. Preferred alkyl groups are those of $C_{20}$ or below. More preferred alkyl groups are those of $C_{13}$ or below. Still more preferred alkyl groups are those of $C_6$ and below. Cycloalkyl is a subset of alkyl and includes cyclic hydrocarbon groups of from 3 to 13 carbon atoms. Examples of cycloalkyl groups include c-propyl, c-butyl, c-pentyl, norbornyl, adamantyl and the like. In this application, alkyl refers to alkanyl, alkenyl and alkynyl residues; it is intended to include cyclohexylmethyl, vinyl, allyl, isoprenyl and the like. Alkylene is another subset of alkyl, referring to the same residues as alkyl, but having two points of attachment. Examples of alkylene include ethylene (—$CH_2CH_2$—), propylene (—$CH_2CH_2CH_2$—), dimethylpropylene (—$CH_2C(CH_3)_2CH_2$—) and cyclohexylpropylene (—$CH_2CH_2CH(C_6H_{13})$—). When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

The term "alkoxy" or "alkoxyl" refers to the group —O-alkyl, preferably including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

The term "substituted alkoxy" refers to the group —O-(substituted alkyl). One preferred substituted alkoxy group is "polyalkoxy" or —O-(optionally substituted alkylene)-(optionally substituted alkoxy), and includes groups such as —$OCH_2CH_2OCH_3$, and glycol ethers such as polyethyleneglycol and —$O(CH_2CH_2O)_xCH_3$, where x is an integer of about 2-20, preferably about 2-10, and more preferably about 2-5. Another preferred substituted alkoxy group is hydroxyalkoxy or —$OCH_2(CH_2)_yOH$, where y is an integer of about 1-10, preferably about 14.

"Acyl" refers to groups of from 1 to 10 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. "Lower-acyl" refers to groups containing one to four carbons and "acyloxy" refers to the group O-acyl.

The term "amino" refers to the group —$NH_2$. The term "substituted amino" refers to the group —NHR or —NRR where each R is independently selected from the group: optionally substituted alkyl, optionally substituted alkoxy, optionally substituted amino, optionally substituted aryl, optionally substituted heteroaryl, optionally substituted heterocyclyl, acyl, alkoxycarbonyl, sulfanyl, sulfinyl and sulfonyl, e.g., diethylamino, methylsulfonylamino, furanyl-oxy-sulfonamino.

"Aryl" means a 5- or 6-membered aromatic ring, a bicyclic 9- or 10-membered aromatic ring system, or a tricyclic 12- to 14-membered aromatic ring system. Examples include cyclopenta-1,3-diene, phenyl, naphthyl, indane, tetraline, fluorene, cyclopenta[b]naphthalene and anthracene.

"Aralkoxy" refers to the group —O-aralkyl. Similarly, "heteroaralkoxy" refers to the group —O-heteroaralkyl; "aryloxy" refers to —O-aryl; and "heteroaryloxy" refers to the group —O-heteroaryl.

"Aralkyl" refers to a residue in which an aryl moiety is attached to the parent structure via an alkyl residue. Examples include benzyl, phenethyl, phenylvinyl, phenylallyl and the like. "Heteroaralkyl" refers to a residue in which a heteroaryl moiety is attached to the parent structure via an alkyl residue. Examples include furanylmethyl, pyridinylmethyl, pyrimidinylethyl and the like.

"ATPase" refers to an enzyme that hydrolyzes ATP. ATPases include proteins comprising molecular motors such as the myosins.

"Halogen" or "halo" refers to fluorine, chlorine, bromine or iodine. Fluorine, chlorine and bromine are preferred. Dihaloaryl, dihaloalkyl, trihaloaryl etc. refer to aryl and alkyl substituted with a plurality of halogens, but not necessarily a plurality of the same halogen; thus 4-chloro-3-fluorophenyl is within the scope of dihaloaryl.

"Heteroaryl" means a 5- or 6-membered aromatic ring containing 14 heteroatoms, a bicyclic 8-, 9- or 10-membered aromatic ring system containing 14 (or more) heteroatoms, or a tricyclic 11- to 14-membered aromatic ring system containing 1-4 (or more) heteroatoms; the heteroatoms are selected from O, N and S. Examples include furan, pyrrole, thiophene, pyrazole, imidazole, triazole, tetrazole, dithiole, oxazole, isoxazole, oxadiazole, thiazole, thiopyran, pyridine, pyridazine, pyrimidine, pyrazine, indole, benzofuran, benzothiophene, quinoline, isoquinoline and quinoxaline.

"Heterocycle" or "heterocyclyl" refers to a cycloalkyl residue in which one to four of the carbons is replaced by a heteroatom such as oxygen, nitrogen or sulfur a 4-, 5-, 6- or 7-membered non-aromatic ring containing 14 heteroatoms, a bicyclic 8-, 9- or 10-membered non-aromatic ring system containing 14 (or more) heteroatoms, or a tricyclic 1'- to 14-membered non-aromatic ring system containing 1-4 (or more) heteroatoms; the heteroatoms are selected from O, N and S. Examples include pyrrolidine, tetrahydrofuran, tetrahydro-thiophene, thiazolidine, piperidine, tetrahydro-pyran, tetrahydro-thiopyran, piperazine, morpholine, thiomorpholine and dioxane. Heterocyclyl also includes ring systems including unsaturated bonds, provided the number and placement of unsaturation does not render the group aromatic. Examples include imidazoline, oxazoline, tetrahydroisoquinoline, benzodioxan, benzodioxole and 3,5-dihydrobenzoxazinyl. Examples of substituted heterocyclyl include 4-methyl-1-piperazinyl and 4-benzyl-1-piperidinyl.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(.±.)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)— or (S)—. The present invention is meant to include all such possible isomers, including racemic mixtures, optically pure forms and intermediate mixtures. Optically active (R)— and (S)—, isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "pharmaceutically acceptable salt" refers to salts that retain the biological effectiveness and properties of the compounds of this invention and, which are not biologically or otherwise undesirable. In many cases, the compounds of this invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

The term "solvate" refers to a compound (e.g., a compound of Formula I or a pharmaceutically acceptable salt thereof) in physical association with one or more molecules of a pharmaceutically acceptable solvent. It will be understood that phrases such as "a compound of Formula I or a pharmaceutically acceptable salt or solvate thereof" are intended to encompass the compound of Formula I, a pharmaceutically acceptable salt of the compound, a solvate of the compound, and a solvate of a pharmaceutically acceptable salt of the compound.

"Substituted-" alkyl, aryl, heteroaryl and heterocyclyl refer respectively to alkyl, aryl, heteroaryl and heterocyclyl wherein one or more (up to about 5, preferably up to about 3) hydrogen atoms are replaced by a substituent independently selected from the group: acyl, optionally substituted alkyl (e.g., fluoroalkyl), optionally substituted alkoxy, alkylenedioxy (e.g. methylenedioxy), optionally substituted amino (e.g., alkylamino and dialkylamino), optionally substituted amidino, optionally substituted aryl (e.g., phenyl), optionally substituted aralkyl (e.g., benzyl), optionally substituted aryloxy (e.g., phenoxy), optionally substituted aralkoxy (e.g., benzyloxy), carboxy (—COOH), acyloxy (—OOCR), alkoxycarbonyl (i.e., esters or —COOR), aminocarbonyl, benzyloxycarbonylamino (CBZ-amino), cyano, carbonyl, halogen, hydroxy, optionally substituted heteroaryl, optionally substituted heteroaralkyl, optionally substituted heteroaryloxy, optionally substituted heteroaralkoxy, nitro, sulfanyl, sulfinyl, sulfonyl, and thio.

The term "sulfanyl" refers to the groups: —S-(optionally substituted alkyl), —S-(optionally substituted aryl), —S-(optionally substituted heteroaryl), and —S-(optionally substituted heterocyclyl).

The term "sulfinyl" refers to the groups: —S(O)—H, —S(O)-(optionally substituted alkyl), —S(O)-(optionally substituted amino), —S(O)-(optionally substituted aryl), —S(O)-(optionally substituted heteroaryl), and —S(O)-(optionally substituted heterocyclyl).

The term "sulfonyl" refers to the groups: —S(O$_2$)—H, —S(O$_2$)-(optionally substituted alkyl), —S(O$_2$)-(optionally substituted amino), —S(O$_2$)-(optionally substituted aryl), —S(O$_2$)-(optionally substituted heteroaryl), —S(O$_2$)-(optionally substituted heterocyclyl), —S(O$_2$)-(optionally substituted alkoxy), —S(O$_2$)-optionally substituted aryloxy), —S(O$_2$)-(optionally substituted heteroaryloxy), and —S(O$_2$)-(optionally substituted heterocyclyloxy).

The term "therapeutically effective amount" or "effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the particular compound of Formula I chosen, the dosing regimen to be followed, timing of administration, the manner of administration and the like, all of which can readily be determined by one of ordinary skill in the art.

The term "treatment" or "treating" means any treatment of a disease in a mammal, including:

a) preventing the disease, that is, causing the clinical symptoms of the disease not to develop;

b) inhibiting the disease, that is, slowing or arresting the development of clinical symptoms; and/or c) relieving the disease, that is, causing the regression of clinical symptoms Compounds of the Present Invention The present invention is directed to the compounds that are selective modulators of the cardiac sarcomere (e.g., by stimulating or otherwise potentiating the activity of cardiac myosin), as represented by Formula I:

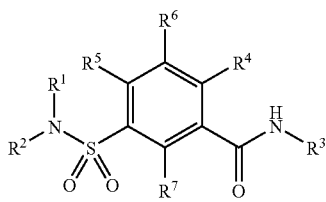

Formula I wherein:

$R^1$ and $R^1$ are independently selected from the group consisting of hydrogen, optionally substituted alkyl, optionally substituted aryl, optionally substituted heteroaryl, optionally substituted aralkyl, and optionally substituted heteroaralkyl; or $R^1$, $R^2$ and the nitrogen to which they are attached form an optionally substituted 5-, 6-, or 7-membered heterocyclic ring;

$R^3$ is optionally substituted aryl or optionally substituted heteroaryl;

$R^4$ is halogen;

$R^5$ is hydrogen, halogen, hydroxy, or optionally substituted lower alkyl; and $R^6$ and $R^7$ are independently selected from the group consisting of hydrogen, halogen, hydroxy, and optionally substituted lower alkyl;

including single stereoisomers, mixtures of stereoisomers, and the pharmaceutically acceptable salts thereof. The compounds of Formula I are useful as active agents in practice of the methods of treatment and in manufacture of the pharmaceutical formulations of the invention, and as intermediates in the synthesis of such active agents.

Nomenclature

The compounds of Formula I can be named and numbered (e.g., using AutoNom version 2.2) as described below. For example, the compound:

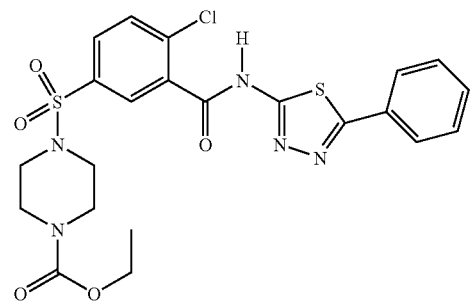

i.e., the compound according to Formula I where $R^1$ and $R^2$ together with the nitrogen to which they are attached form a substituted piperazine ring; $R^3$ is a substituted thiadiazole ring; $R^4$ is chloro; and $R^5$, $R^6$, and $R^7$ are hydrogen can be named 4-[4-chloro-3-(5-phenyl-[1,3,4]thiadiazol-2-ylcarbamoyl)-benzenesulfonyl]-piperazine-1-carboxylic acid ethyl ester.

Likewise, the compound:

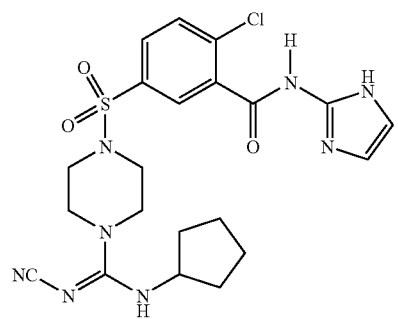

i.e., the compound according to Formula I where $R^1$ and $R^2$ together with the imidazole ring; $R^4$ is chloro; and $R^5$, $R^6$, and $R^7$ are hydrogen can be named 2-chloro-5-[4-(N-cyclopentyl-N'-cyano-carbamimidoyl)-piperazine-1-sulfonyl]-N-(1H-imidazol-2-yl)-benzamide.

Synthesis of the Compounds of Formula I

The compounds of the invention can be synthesized utilizing techniques well known in the art, e.g., as illustrated below with reference to the Reaction Schemes.

Synthetic Reaction Parameters

Unless specified to the contrary, the reactions described herein take place at atmospheric pressure, generally within a temperature range from −10° C. to 110° C. Further, except as employed in the Examples or as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

The terms "solvent", "organic solvent" or "inert solvent" each mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

When desired, the (R)- and (S)-isomers may be resolved by methods known to those skilled in the art, for example by formation of diastereoisomeric salts or complexes which may be separated, for example, by crystallization; via formation of diastereoisomeric derivatives which may be separated, for example, by cyrstallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. For example, a compound of Formula I can be dissolved in a lower alkanol and placed on a Chiralpak AD (205×20 mm) column (Chiral Technologies, Inc.) conditioned for 60 min at 70% EtOAc in Hexane. It will be appreciated that where the desired enantiomer is converted into another chemical entity by one of the separation procedures described above, a further step may be required to liberate the desired enantiomeric form. Alternatively, a specific enantiomer may be synthesized by asymmetric synthesis using optically active reagents, substrates, catalysts or solvents, or by converting one enantiomer to the other by asymmetric transformation.

Starting Materials

The optionally substituted benzoic acids of Formula 101 are commercially available, e.g., from Acros Organic or Aldrich Chemical Company, Milwaukee, Wis., or may be readily prepared by those skilled in the art using commonly employed synthetic methodology. One of skill in the art will appreciate that the commercially available compounds may lack a carboxylprotecting group PG. Other reactants are likewise commercially available or may be readily prepared by those skilled in the art using commonly employed synthetic methodology.

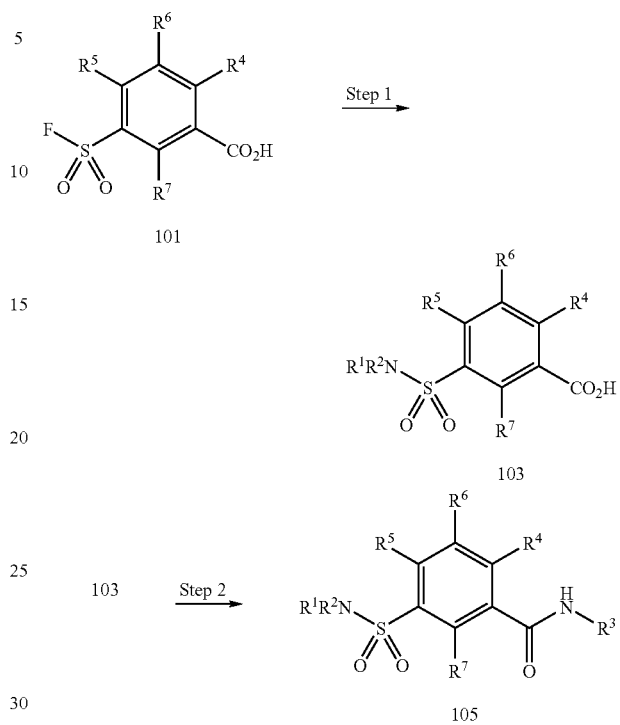

Preparation of Compounds of Formula 103

Referring to Reaction Scheme 1, Step 1, a compound of Formula 101 is placed in a vial. The vial is flushed with nitrogen and a positive pressure is maintained. An anhydrous, nonpolar solvent, such as dichloromethane is added, followed by an excess (preferably about 1.2 equivalents) of a compound of formula $R^1R^2NH$ and a base such as ethyldiisopropylamine. The mixture is stirred for about 1.5 hours after which time an additional aliquot (preferably about 0.8 equivalent) of the amine of formula $R^1R^2NH$ is added. After about 14 hours the mixture is analyzed by reverse-phase HPLC-MS in negative ionization mode. If the sulfonyl fluoride starting material is present, an additional amount (preferably about 0.35 equivalent) of the amine of formula $R^1R^2NH$ and ethyldiisopropylamine are added and the mixture is stirred for about 4 hours. This may be repeated again as necessary. The resulting product, a compound of Formula 103, can be recovered by conventional methods, such as chromatography, filtration, evaporation, crystallization, and the like or, alternatively, used in the next step without purification and/or isolation. It should be noted that addition of excess nucleophilic amine at the beginning of the reaction may result in significant bis addition, giving sulfonamide and carboxamide product. Stepwise addition of nucleophilic amine as needed suppresses formation of this side product.

Preparation of Compounds of Formula 105

Referring to Reaction Scheme 1, Step 2, a compound of Formula 103 is placed in a vial along with an excess (preferably about 1.2 equivalents) of a compound of Formula $R^3NH_2$, an excess (preferably about 1.5 equivalents) of HBTU and an excess (preferably about 1.5 equivalents) of HOBt hydrate. The vial is flushed with nitrogen and a positive pressure is maintained. An anhydrous solvent, such as dimethylformamide is added, followed by a base such as ethyldiisopropylamine and the mixture is stirred for about 14 hours. The resulting product, a compound of Formula 105, can be recovered by conventional methods, such as chromatography, filtration, evaporation, crystallization, and the like or, alternatively, used in the next step without purification and/or isolation.

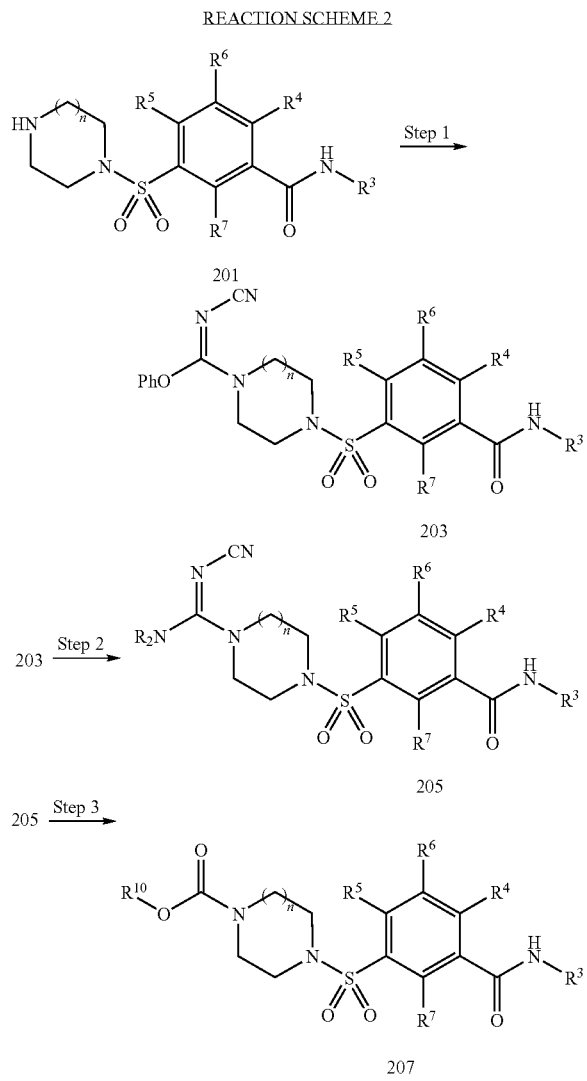

Preparation of Compounds of Formula 203

Referring to Reaction Scheme 2, Step 1, an excess (preferably about 10 equivalents) of diphenylcyanocarbonimidate is added to a compound of Formula 201 wherein n is 1 or 2. The vial is capped, flushed with nitrogen and a positive pressure is maintained. Anhydrous, inert solvent such as THF is added, followed by a base such as ethyldiisopropylamine. The mixture is stirred for about one hour. The resulting product, a compound of Formula 203, can be recovered by conventional methods, such as chromatography, filtration, evaporation, crystallization, and the like or, alternatively, used in the next step without purification and/or isolation.

Preparation of Compounds of Formula 205

Referring to Reaction Scheme 2, Step 2, a compound of Formula 203 is placed in a vial. The vial is flushed with nitrogen and a positive pressure is maintained. An anhydrous inert solvent such as THF is added followed by an excess (especially about five equivalents) of an amine of formula $R^{10}NH_2$ wherein $R^{10}$ is optionally substituted alkyl, optionally substituted aryl, optionally substituted aralkyl, optionally substituted heteroaryl, or optionally substituted heteroaralkyl. The mixture is stirred until the reaction is complete. The resulting product, a compound of Formula 205, can be recovered by conventional methods, such as chromatography, filtration, evaporation, crystallization, and the like or, alternatively, used in the next step without purification and/or isolation.

Compounds prepared by the above-described processes of the invention can be identified, e.g., by the presence of a detectable amount of one or more of the starting materials or reagents. While it is well known that pharmaceuticals must meet pharmacopoeia standards before approval and/or marketing, and that synthetic reagents (such as the various substituted amines or alcohols) and precursors should not exceed the limits prescribed by pharmacopoeia standards, final compounds prepared by a process of the present invention may have minor, but detectable, amounts of such materials present, for example at levels in the range of 95% purity with no single impurity greater than 1%. These levels can be detected, e.g., by emission spectroscopy. It is important to monitor the purity of pharmaceutical compounds for the presence of such materials, which presence is additionally disclosed as a method of detecting use of a synthetic process of the invention.

Particular Processes and Last Steps

A racemic mixture of isomers of a compound of Formula I is placed on a chromatography column and separated into (R)- and (S)-enantiomers.

A compound of Formula I is contacted with a pharmaceutically acceptable acid to form the corresponding acid addition salt.

A pharmaceutically acceptable acid addition salt of Formula I is contacted with a base to form the corresponding free base of Formula I.

Particular Compounds

Provided for the compounds, pharmaceutical formulations, methods of manufacture and use of the present invention are the following combinations and permutations of substituent groups of Formula I. Particular embodiments of the invention include or employ the compounds of Formula I having the following combinations and permutations of substituent groups. These are presented in support of the appended claims to support other combinations and permutations of substituent groups, which for the sake of brevity have not been specifically claimed, but should be appreciated as encompassed within the teachings of the present disclosure.

$R^1$ and $R^2$

When referring to compounds of Formula I, in a particular embodiment, $R^1$ and $R^2$ are independently selected from the group consisting of hydrogen, optionally substituted alkyl, optionally substituted aryl, optionally substituted heteroaryl, optionally substituted aralkyl, and optionally substituted heteroaralkyl. [Brad—any sub-preferences for the non-cyclic version?]

When referring to compounds of Formula I, in another particular embodiment, $R^1$, $R^2$ and the nitrogen to which they are attached form an optionally substituted 5-, 6-, or 7-membered heterocyclic ring. In a more particular embodiment, $R^1$, $R^2$ and the nitrogen to which they are attached form a piperidin-1-yl; piperazin-1-yl; moroholin-4-yl; pyrrolidin-1-yl; thiomorpholin-4-yl or diazepan-1-yl, which optionally is substituted with one, two or three of the following groups: optionally substituted alkyl, halogen, hydroxy, alkoxy, alkylenedioxy (e.g. methylenedioxy), carboxy (—COOH), optionally substituted acyloxy (RCOO—), optionally substituted alkoxycarbonyl- (—COOR), optionally substituted aminocarbonyl, cyano, optionally substituted acyl, oxo, nitro, optionally substituted amino, sulfanyl, sulfinyl, sulfonyl, optionally substituted aminosulfonyl-, amidino, phenyl, benzyl, heteroaryl, heterocyclyl, substituted heterocyclyl, aryloxy, arallkoxy, heteroaryloxy, and heteroaralkoxy.

When $R^1$, $R^1$ and the nitrogen to which they are attached form an optionally substituted diazepan-1-yl ring, in a particular embodiment, the diazepane nitrogen is further substituted with optionally substituted acyl, optionally substituted alkoxycarbonyl, or optionally substituted aminosulfonyl.

When $R^1$, $R^2$ and the nitrogen to which they are attached form an optionally substituted piperazin-1-yl ring, in a particular embodiment, the piperazine nitrogen is further substituted with hydrogen, an optionally substituted acyl, optionally substituted alkoxycarbonyl, optionally substituted aminosulfonyl, optionally substituted heteroaryl, optionally substituted alkyl, or optionally substituted sulfonyl.

When $R^1$, $R^2$ and the nitrogen to which they are attached form an optionally substituted piperadin-1-yl ring, in a particular embodiment, the piperidine ring is further substituted with hydrogen, optionally substituted alkoxycarbonyl, optionally substituted aminocarbonyl, optionally substituted amino, hydroxy, optionally substituted alkoxy, or alkylenedioxy.

When $R^1$, $R^2$ and the nitrogen to which they are attached form an optionally substituted pyrrolidin-1-yl ring, in a particular embodiment, the pyrrolidine ring is further substituted with optionally substituted amino.

$R^3$

When referring to compounds of Formula I, in a particular embodiment, $R^3$ is optionally substituted aryl or optionally substituted heteroaryl. More particularly, $R^3$ is phenyl, isoxazolyl, oxazolyl, pyridinyl, pyrazinyl, pyrimidinyl, tetrazol-5-yl, thiazolyl, thiadiazolyl or imidazolyl, which is optionally substituted with a halogen, lower alkoxy, an optionally substituted aryl or heteroaryl group.

In one particular embodiment, $R^3$ is phenyl which is optionally substituted with halogen (especially fluoro) or lower alkoxy (especially methoxy). In another particular embodiment, $R^3$ is a heteroaryl group which is optionally substituted with an optionally substituted aryl or heteroaryl group. Yet more particularly, $R^3$ is [1,3,4]thiadiazol-2-yl which is optionally substituted with an optionally substituted phenyl group or $R^3$ is 1H-imidazol-2-yl. In a most particular embodiment, $R^3$ is oxazol-2-yl, 5-phenyl-[1,3,4]thiadiazol-2-yl or 1H-imidazol-2-yl.

$R^4$

When referring to compounds of Formula I, in a particular embodiment, $R^4$ is halogen. More particularly, $R^4$ is chloro.

$R^5$, $R^6$, and $R^7$

When referring to compounds of Formula I, in a particular embodiment, $R^5$ is hydrogen, halogen, hydroxy, or optionally substituted lower alkyl; and $R^6$ and $R^7$ are independently selected from the group consisting of hydrogen, hydrogen, halogen, hydroxy, and optionally substituted lower alkyl. In another embodiment, $R^5$, $R^6$ and $R^7$ are hydrogen.

Particular Subgenus

When considering the compounds of Formula I, in a particular embodiment,
$R^1$, $R^2$ and the nitrogen to which they are attached form an optionally substituted 5-, 6-, or 7-membered heterocyclic ring;
$R^3$ is optionally substituted aryl or optionally substituted heteroaryl;
$R^4$ is halogen; and
$R^5$, $R^7$ and $R^7$ are hydrogen.

In another particular embodiment,
$R^1$, $R^2$ and the nitrogen to which they are attached form an optionally substituted 5-, 6-, or 7-membered heterocyclic ring;
$R^3$ is optionally substituted aryl or optionally substituted heteroaryl;
$R^4$ is chloro; and
$R^5$, $R^6$ and $R^7$ are hydrogen.

In another particular embodiment,
$R^1$, $R^2$ and the nitrogen to which they are attached form an optionally substituted 5-, 6-, or 7-membered heterocyclic ring;
$R^3$ is [1,3,4]thiadiazol-2-yl which is optionally substituted with an optionally substituted phenyl group or $R^3$ is 1H-imidazol-2-yl group;
$R^4$ is a halogen; and
$R^5$, $R^7$ and $R^7$ are hydrogen.

In another particular embodiment,
$R^1$, $R^2$ and the nitrogen to which they are attached form an optionally substituted 5-, 6-, or 7-membered heterocyclic ring;
$R^3$ is [1,3,4]thiadiazol-2-yl which is optionally substituted with an optionally substituted phenyl group or $R^3$ is a 1H-imidazol-2-yl group;
$R^4$ is chloro; and
$R^5$, $R^6$ and $R^7$ are hydrogen.

In another particular embodiment,
$R^1$, $R^2$ and the nitrogen to which they are attached form an optionally substituted 5-, 6-, or 7-membered heterocyclic ring;
$R^3$ is 5-phenyl-[1,3,4]thiadiazol-2-yl or 1H-imidazol-2-yl;
$R^4$ is halogen; and
$R^5$, $R^5$ and $R^7$ are hydrogen.

In another particular embodiment,
$R^1$, $R^2$ and the nitrogen to which they are attached form an optionally substituted 5-, 6-, or 7-membered heterocyclic ring;
$R^3$ is 5-phenyl-[1,3,4]thiadiazol-2-yl or 1H-imidazol-2-yl;
$R^4$ is chloro; and
$R^5$, $R^6$ and $R^7$ are hydrogen.

Particular compounds include

| X | $R^8$ | $R^9$ | $R^3$ | $R^4$ | $R^5$ | $R^6$ | $R^7$ |
|---|---|---|---|---|---|---|---|
| $CHR^9NR^8$ | t-Butoxycarbonyl- | H | 1H-imidazol-2-yl | Cl | H | H | H |
| $CHR^9NR^8$ | Acetyl- | H | 1H-imidazol-2-yl | Cl | H | H | H |

-continued

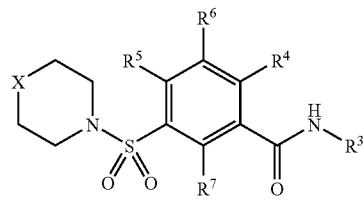

| X | R8 | R9 | R3 | R4 | R5 | R6 | R7 |
|---|---|---|---|---|---|---|---|
| CHR9NR8 | i-Propoxycarbonyl- | H | 1H-imidazol-2-yl | Cl | H | H | H |
| CHR9NR8 | Methoxycarbonyl- | H | 1H-imidazol-2-yl | Cl | H | H | H |
| CHR9NR8 | 3-Methylbutanoyl- | H | 1H-imidazol-2-yl | Cl | H | H | H |
| CHR9NR8 | Isobutyryl- | H | 1H-imidazol-2-yl | Cl | H | H | H |
| CHR9NR8 | Cyclopropylacetyl- | H | 1H-imidazol-2-yl | Cl | H | H | H |
| CHR9NR8 | Dimethylaminosulfonyl- | H | 1H-imidazol-2-yl | Cl | H | H | H |
| CHR9NR8 | sec-Butoxycarbonyl- | H | 1H-imidazol-2-yl | Cl | H | H | H |
| CHR9NR8 | Propanoyl- | H | 1H-imidazol-2-yl | Cl | H | H | H |
| CHR9NR8 | Cyclohexyloxycarbonyl- | H | 1H-imidazol-2-yl | Cl | H | H | H |
| CHR9NR8 | Acetyl- | H | 5-Phenyl-[1,3,4]thiadiazol-2-yl | Cl | H | H | H |
| CR9R8 | Hydrogen | H | 5-Phenyl-[1,3,4]thiadiazol-2-yl | Cl | H | H | H |
| CR9R8 | Hydrogen | H | 5-Phenyl-[1,3,4]thiadiazol-2-yl | Cl | H | H | H |
| CR9R8 | Methoxycarbonyl- | H | 5-Phenyl-[1,3,4]thiadiazol-2-yl | Cl | H | H | H |
| CR9R8 | Hydrogen | H | 1H-imidazol-2-yl | Cl | H | H | H |
| CR9R8 | Carbamoyl- | H | 1H-imidazol-2-yl | Cl | H | H | H |
| CR9R8 | Methoxycarbonyl- | H | 1H-imidazol-2-yl | Cl | H | H | H |
| CR9R8 | N-(t-butoxycarbonyl)-N-methylamino- | H | 1H-imidazol-2-yl | Cl | H | H | H |
| CR9R8 | Acetamido- | H | 1H-imidazol-2-yl | Cl | H | H | H |
| CR9R8 | N-acetyl-N-methylamino- | H | 1H-imidazol-2-yl | Cl | H | H | H |
| CR9R8 | Methylaminocarbonyl- | H | 1H-imidazol-2-yl | Cl | H | H | H |
| CR9R8 | Ethoxycarbonyl- | H | 1H-imidazol-2-yl | Cl | H | H | H |
| CR9R8 | OH | H | 1H-imidazol-2-yl | Cl | H | H | H |
| CR9R8 | N-(t-butoxycarbonyl)amino- | H | 5-Phenyl-[1,3,4]thiadiazol-2-yl | Cl | H | H | H |
| CR9R8 | Methoxycarbonyl- | H | 5-Phenyl-[1,3,4]thiadiazol-2-yl | Cl | H | H | H |
| CR9R8 | Carbamoyl- | H | 5-Phenyl-[1,3,4]thiadiazol-2-yl | Cl | H | H | H |
| CR9R8 | Hydroxy- | H | 5-Phenyl-[1,3,4]thiadiazol-2-yl | Cl | H | H | H |
| CR9R8 | Ethylenedioxy- | H | 5-Phenyl-[1,3,4]thiadiazol-2-yl | Cl | H | H | H |
| CR9R8 | Ethylenedioxy- | H | 1H-imidazol-2-yl | Cl | H | H | H |
| CR9R8 | Ethylenedioxy- | H | 5-Phenyl-[1,3,4]thiadiazol-2-yl | Cl | H | H | H |
| NR8 | Ethoxycarbonyl- | — | 5-Phenyl-[1,3,4]thiadiazol-2-yl | Cl | H | H | H |

-continued

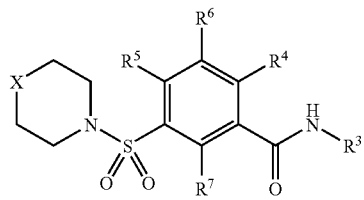

| X | R8 | R9 | R3 | R4 | R5 | R6 | R7 |
|---|---|---|---|---|---|---|---|
| NR8 | Acetyl- | — | 5-Phenyl-[1,3,4]thiadiazol-2-yl | Cl | H | H | H |
| NR8 | Methoxycarbonyl- | — | 5-Phenyl-[1,3,4]thiadiazol-2-yl | Cl | H | H | H |
| NR8 | Methoxyacetyl- | — | 5-Phenyl-[1,3,4]thiadiazol-2-yl | Cl | H | H | H |
| NR8 | 3-Methylbutanoyl- | — | 5-Phenyl-[1,3,4]thiadiazol-2-yl | Cl | H | H | H |
| NR8 | Propoxycarbonyl- | — | 5-Phenyl-[1,3,4]thiadiazol-2-yl | Cl | H | H | H |
| NR8 | i-Propoxycarbonyl- | — | 5-Phenyl-[1,3,4]thiadiazol-2-yl | Cl | H | H | H |
| NR8 | Dimethylaminocarbonyl- | — | 5-Phenyl-[1,3,4]thiadiazol-2-yl | Cl | H | H | H |
| NR8 | Propoxycarbonyl- | — | 1H-imidazol-2yl | Cl | H | H | H |
| NR8 | sec-Butoxycarbonyl- (especially the R-isomer) | — | 1H-imidazol-2yl | Cl | H | H | H |
| NR8 | 2-Cyclopentylacetyl- | — | 1H-imidazol-2yl | Cl | H | H | H |
| NR8 | 2-Cyclohexylacetyl- | — | 1H-imidazol-2yl | Cl | H | H | H |
| NR8 | Ethoxycarbonyl- | — | 5-Phenyl-[1,3,4]thiadiazol-2-yl | Cl | H | H | H |
| NR8 | Methoxyacetyl- | — | 5-Phenyl-[1,3,4]thiadiazol-2-yl | Cl | H | H | H |
| NR8 | Acetyl- | — | 5-Phenyl-[1,3,4]thiadiazol-2-yl | Cl | H | H | H |
| NR8 | Methyl- | — | 5-Phenyl-[1,3,4]thiadiazol-2-yl | Cl | H | H | H |
| NR8 | Ethoxycarbonyl- | — | Fluorophenyl- | F | H | H | H |
| NR8 | Pyridinyl- | — | Methoxyphenyl- | F | H | H | H |
| NR8 | Methyl- | — | 5-Phenyl-[1,3,4]thiadiazol-2-yl | Cl | H | H | H |
| NR8 | Butyryl- | — | 5-Phenyl-[1,3,4]thiadiazol-2-yl | Cl | H | H | H |
| NR8 | Ethylcarbamoyl- | — | 5-Phenyl-[1,3,4]thiadiazol-2-yl | Cl | H | H | H |
| NR8 | Ethoxycarbonyl- | — | 1H-imidazol-2yl | | | | |
| NR8 | Ethoxycarbonyl- | — | Isoxazol-3-yl | | | | |
| NR8 | Butyl- | — | 5-Phenyl-[1,3,4]thiadiazol-2-yl | Cl | H | H | H |
| NR8 | Formyl- | — | 5-Phenyl-[1,3,4]thiadiazol-2-yl | Cl | H | H | H |
| NR8 | Isobutyryl- | — | 5-Phenyl-[1,3,4]thiadiazol-2-yl | Cl | H | H | H |

| X | R⁸ | R⁹ | R³ | R⁴ | R⁵ | R⁶ | R⁷ |
|---|---|---|---|---|---|---|---|
| NR⁸ | 2,3-Dihydroxy-propionyl- | — | 5-Phenyl-[1,3,4]thiadiazol-2-yl | Cl | H | H | H |
| NR⁸ | (1-hydroxypropan-2-yloxy)carbonyl- | — | 5-Phenyl-[1,3,4]thiadiazol-2-yl | Cl | H | H | H |
| NR⁸ | Ethoxycarbonyl- | — | Oxazol-2-yl | Cl | H | H | H |
| NR⁸ | Ethoxycarbonyl- | — | 2H-tetrazol-5-yl | Cl | H | H | H |
| NR⁸ | t-Butoxycarbonyl- | — | 1H-imidazol-2-yl | Cl | H | H | H |
| NR⁸ | Acetyl- | — | 1H-imidazol-2-yl | Cl | H | H | H |
| NR⁸ | Ethoxycarbonyl- | — | 4-Methyl-1H-imidazol-2-yl | Cl | H | H | H |
| NR⁸ | i-Propoxycarbonyl- | — | 1H-imidazol-2-yl | Cl | H | H | H |
| NR⁸ | Methoxycarbonyl- | — | 1H-imidazol-2-yl | Cl | H | H | H |
| NR⁸ | Butyryl- | — | 1H-imidazol-2-yl | Cl | H | H | H |
| NR⁸ | Dimethylaminocarbonyl- | — | 1H-imidazol-2-yl | Cl | H | H | H |
| NR⁸ | Methoxyacetyl- | — | 1H-imidazol-2-yl | Cl | H | H | H |
| NR⁸ | 2-Methylpropan-1-oxycarbonyl- | — | 1H-imidazol-2-yl | Cl | H | H | H |
| NR⁸ | 3-Methylbutyryl- | — | 1H-imidazol-2-yl | Cl | H | H | H |
| NR⁸ | 2,2-Dimethylpropan-1-oxycarbonyl- | — | 1H-imidazol-2-yl | Cl | H | H | H |
| NR⁸ | Isobutyryl- | — | 1H-imidazol-2-yl | Cl | H | H | H |
| NR⁸ | Ethylsulfonyl- | — | 1H-imidazol-2-yl | Cl | H | H | H |
| NR⁸ | Butoxycarbonyl- | — | 1H-imidazol-2-yl | Cl | H | H | H |
| NR⁸ | Cyclohexyloxycarbonyl- | — | 1H-imidazol-2-yl | Cl | H | H | H |
| NR⁸ | Cyclopentyloxycarbonyl- | — | 1H-imidazol-2-yl | Cl | H | H | H |
| NR⁸ | Formyl- | — | 1H-imidazol-2-yl | Cl | H | H | H |
| NR⁸ | sec-butoxycarbonyl- (especially the S-isomer) | — | 1H-imidazol-2-yl | Cl | H | H | H |
| NR⁸ | Piperidin-1-ylcarbonyl- | — | 1H-imidazol-2-yl | Cl | H | H | H |
| NR⁸ | pyrrolidin-1-ylcarbonyl- | — | 1H-imidazol-2-yl | Cl | H | H | H |
| NR⁸ | 4-methylpiperazin-1-yl-carbonyl- | — | 1H-imidazol-2-yl | Cl | H | H | H |
| NR⁸ | Diethylaminocarbonyl- | — | 1H-imidazol-2-yl | Cl | H | H | H |
| NR⁸ | Ethylaminocarbonyl- | — | 1H-imidazol-2-yl | Cl | H | H | H |
| NR⁸ | Cyclohexylcarbonyl- | — | 1H-imidazol-2-yl | Cl | H | H | H |
| NR⁸ | 2-(tetrahydro-2H-pyran-4-yl)acetyl- | — | 1H-imidazol-2-yl | Cl | H | H | H |
| NR⁸ | 2-(1-(tert-butoxycarbonyl)piperidin-4-yl)acetyl- | — | 1H-imidazol-2-yl | Cl | H | H | H |
| NR⁸ | 2-(piperidin-4-yl)acetyl- | — | 1H-imidazol-2-yl | Cl | H | H | H |
| NR⁸ | Pentanoyl- | — | 1H-imidazol-2-yl | Cl | H | H | H |
| NR⁸ | Cyclopropylacetyl- | — | 1H-imidazol-2-yl | Cl | H | H | H |
| NR⁸ | Propanoyl- | — | 1H-imidazol-2-yl | Cl | H | H | H |
| NR⁸ | 3,3-dimethylbutanoyl- | — | 1H-imidazol-2-yl | Cl | H | H | H |
| NR⁸ | Cyclopentylcarbonyl- | — | 1H-imidazol-2-yl | Cl | H | H | H |
| NR⁸ | t-butoxycarbonyl- | — | 4,5-Dihydro-5-oxo-1H-imidazol-2-yl | Cl | H | H | H |
| NR⁸ | Cyclopropylcarbonyl- | — | 1H-imidazol-2-yl | Cl | H | H | H |
| NR⁸ | Ethoxyacetyl- | — | 1H-imidazol-2-yl | Cl | H | H | H |
| NR⁸ | Benzyloxyacetyl- | — | 1H-imidazol-2-yl | Cl | H | H | H |
| NR⁸ | tetrahydrofuran-2-ylcarbonyl- | — | 1H-imidazol-2-yl | Cl | H | H | H |
| NR⁸ | Dimethylaminosulfonyl- | — | 1H-imidazol-2-yl | Cl | H | H | H |
| NR⁸ | N-(t-butoxycarbonyl)aminosulfonyl- | — | 1H-imidazol-2-yl | Cl | H | H | H |
| NR⁸ | Aminosulfonyl- | — | 1H-imidazol-2-yl | Cl | H | H | H |
| NR⁸ | t-butoxycarbonyl- | — | Pyrazin-2-yl | Cl | H | H | H |
| NR⁸ | t-butoxycarbonyl- | — | Pyridinyl | Cl | H | H | H |
| NR⁸ | t-butoxycarbonyl- | — | Methyl-pyridinyl- | Cl | H | H | H |
| NR⁸ | t-butoxycarbonyl- | — | Isoxazol-3-yl | Cl | H | H | H |
| NR⁸ | Methoxycarbonyl- | — | 1H-imidazol-2-yl | Cl | H | H | H |
| NR⁸ | Acetyl- | — | Pyridinyl | Cl | H | H | H |
| NR⁸ | Methoxycarbonyl- | — | Pyridinyl | Cl | H | H | H |
| NR⁸ | t-butoxycarbonyl- | — | 5-Phenyl-[1,3,4]thiadiazol-2-yl | Cl | H | H | H |
| NR⁸CH₂ | 2-cyclohexylacetyl- | — | 1H-imidazol-2yl | Cl | H | H | H |
| NR⁸CH₂ | sec-butoxycarbonyl- (especially the S-isomer) | — | 1H-imidazol-2yl | Cl | H | H | H |
| NR⁸CH₂ | Ethoxycarbonyl- | — | 5-Phenyl-[1,3,4]thiadiazol-2-yl | Cl | H | H | H |
| NR⁸CH₂ | Isobutyryl- | — | 5-Phenyl-[1,3,4]thiadiazol-2-yl | Cl | H | H | H |
| NR⁸CH₂ | Methoxycarbonyl- | — | 5-Phenyl-[1,3,4]thiadiazol-2-yl | Cl | H | H | H |
| NR⁸CH₂ | Isobutyryl- | — | 5-Phenyl-[1,3,4]thiadiazol-2-yl | Cl | H | H | H |
| NR⁸CH₂ | Formyl- | — | 5-Phenyl-[1,3,4]thiadiazol-2-yl | Cl | H | H | H |
| O | — | — | 5-Phenyl-[1,3,4]thiadiazol-2-yl | Cl | H | H | H |
| O | — | — | 5-Phenyl-[1,3,4]thiadiazol-2-yl | Cl | H | H | H |
| O | — | — | 1H-imidazol-2yl | Cl | H | H | H |
| O | — | — | Thiazol-2-yl | Cl | H | H | H |
| O | — | — | Thiazol-2-yl | Cl | H | H | H |
| O | — | — | 5-Phenyl-[1,3,4]thiadiazol-2-yl | Cl | H | H | H |
| O | — | — | 5-(p-Chlorophenyl)-[1,3,4]thiadiazol-2-yl | Cl | H | H | H |

-continued

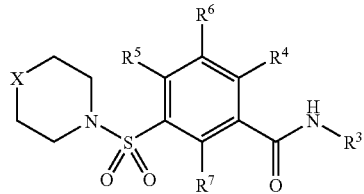

| X | R⁸ | R⁹ | R³ | R⁴ | R⁵ | R⁶ | R⁷ |
|---|---|---|---|---|---|---|---|
| O | — | — | 5-Phenyl-[1,3,4]thiadiazol-2-yl | F | H | H | H |
| O | — | — | 1H-imidazol-2yl | Cl | H | H | H |
| O | — | — | 5-phenyl-1H-imidazol-2-yl | Cl | H | H | H |
| O | — | — | 5-phenylpyrimidin-2-yl | Cl | H | H | H |
| S | — | — | 1H-imidazol-2-yl | Cl | H | H | H |

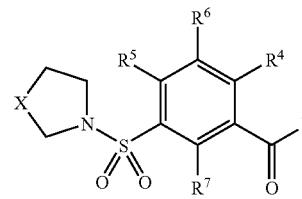

| X | R⁸ | R³ | R⁴ | R⁵ | R⁶ | R⁷ |
|---|---|---|---|---|---|---|
| CHR⁸ | N-methyl-N-acetyl-amino- | 1H-imidazol-2-yl | Cl | H | H | H |
| CHR⁸ | N-(t-butoxycarbonyl)-N-methylamino- | 1H-imidazol-2-yl | Cl | H | H | H |
| CHR⁸ | Hydrogen | 1H-imidazol-2-yl | Cl | H | H | H |
| CHR⁸ | N-(Dimethylaminocarbonyl)-N-methyl-amino- | 5-Phenyl-[1,3,4]thiadiazol-2-yl | Cl | H | H | H |
| CHR⁸ | N-(3-methylbutyrl)-N-methylamino- | 5-Phenyl-[1,3,4]thiadiazol-2-yl | Cl | H | H | H |
| CHR⁸ | N-(Propoxycarbonyl)-N-methylamino- | 5-Phenyl-[1,3,4]thiadiazol-2-yl | Cl | H | H | H |
| CHR⁸ | N-(i-propoxycarbonyl)-N-methylamino- | 5-Phenyl-[1,3,4]thiadiazol-2-yl | Cl | H | H | H |
| CHR⁸ | N-butyryl-N-methylamino- | 5-Phenyl-[1,3,4]thiadiazol-2-yl | Cl | H | H | H |
| CHR⁸ | N-(ethoxycarbonyl)-N-methylamino- | 5-Phenyl-[1,3,4]thiadiazol-2-yl | Cl | H | H | H |
| CHR⁸ | N-(Ethoxycarbonyl)-amino- | 5-Phenyl-[1,3,4]thiadiazol-2-yl | Cl | H | H | H |
| CHR⁸ | N-(isopropoxycarbonyl)-amino- | 5-Phenyl-[1,3,4]thiadiazol-2-yl | Cl | H | H | H |
| CHR⁸ | N-(methoxycarbonyl)-amino- | 5-Phenyl-[1,3,4]thiadiazol-2-yl | Cl | H | H | H |

More particularly, compounds of the invention include

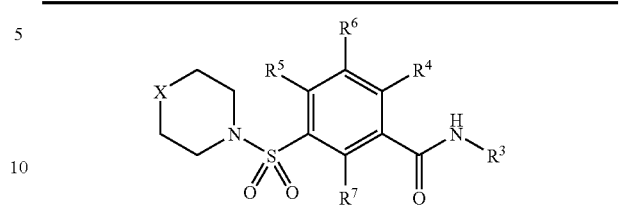

| X | R⁸ | R⁹ | R³ | R⁴ | R⁵ | R⁶ | R⁷ |
|---|---|---|---|---|---|---|---|
| CHR⁸ | Methoxycarbonyl- | H | 5-Phenyl-[1,3,4]thiadiazol-2-yl | Cl | H | H | H |
| CR⁹R⁸ | Methylenedioxy- | | 5-Phenyl-[1,3,4]thiadiazol-2-yl | Cl | H | H | H |
| CR⁹R⁸ | Ethylenedioxy- | | 5-Phenyl-[1,3,4]thiadiazol-2-yl | Cl | H | H | H |
| NR⁸ | Ethoxycarbonyl- | — | 5-Phenyl-[1,3,4]thiadiazol-2-yl | Cl | H | H | H |
| NR⁸ | Acetyl- | — | 5-Phenyl-[1,3,4]thiadiazol-2-yl | Cl | H | H | H |
| NR⁸ | Methoxycarbonyl- | — | 5-Phenyl-[1,3,4]thiadiazol-2-yl | Cl | H | H | H |
| NR⁸ | Methoxyacetyl- | — | 5-Phenyl-[1,3,4]thiadiazol-2-yl | Cl | H | H | H |
| NR⁸ | 3-Methyl-butanoyl- | — | 5-Phenyl-[1,3,4]thiadiazol-2-yl | Cl | H | H | H |
| NR⁸ | Propoxycarbonyl- | — | 5-Phenyl-[1,3,4]thiadiazol-2-yl | Cl | H | H | H |
| NR⁸ | i-Propoxycarbonyl- | — | 5-Phenyl-[1,3,4]thiadiazol-2-yl | Cl | H | H | H |
| NR⁸ | Dimethylaminocarbonyl- | — | 5-Phenyl-[1,3,4]thiadiazol-2-yl | Cl | H | H | H |
| NR⁸ | Propoxycarbonyl- | — | 1H-imidazol-2yl | Cl | H | H | H |
| NR⁸ | sec-Butoxycarbonyl- (especially the R-isomer) | — | 1H-imidazol-2yl | Cl | H | H | H |
| NR⁸ | 2-Cyclopentyl-acetyl- | — | 1H-imidazol-2yl | Cl | H | H | H |
| NR⁸ | 2-Cyclohexyl-acetyl- | — | 1H-imidazol-2yl | Cl | H | H | H |
| NR⁸ | Butyryl- | — | 5-Phenyl-[1,3,4]thiadiazol-2-yl | Cl | H | H | H |
| NR⁸ | Ethoxycarbonyl- | —H | 5-Phenyl-[1,3,4]thiadiazol-2-yl | Cl | H | H | H |
| NR⁸ | Methoxyacetyl- | — | 5-Phenyl-[1,3,4]thiadiazol-2-yl | Cl | H | H | H |
| NR⁸ | Acetyl- | — | 5-Phenyl-[1,3,4]thiadiazol-2-yl | Cl | H | H | H |
| NR⁸ | Methyl- | — | 5-Phenyl-[1,3,4]thiadiazol-2-yl | Cl | H | H | H |
| NR⁸CH₂ | Acetyl- | — | 5-Phenyl-[1,3,4]thiadiazol-2-yl | Cl | H | H | H |
| NR⁸CH₂ | 2-Cyclohexyl-acetyl- | — | 1H-imidazol-2yl | Cl | H | H | H |
| NR⁸CH₂ | sec-Butoxycarbonyl- | — | 1H-imidazol-2yl | Cl | H | H | H |

-continued

| X | R8 | R9 | R3 | R4 | R5 | R6 | R7 |
|---|---|---|---|---|---|---|---|
| | (especially the S-isomer) | | | | | | |
| O | — | — | 5-Phenyl-[1,3,4]thiadiazol-2-yl | Cl | H | H | H |
| O | — | — | 5-Phenyl-[1,3,4]thiadiazol-2-yl | Cl | H | H | H |
| O | — | — | 1H-imidazol-2yl | Cl | H | H | H |
| O | — | — | Thiazol-2-yl | Cl | H | H | H |

Utility, Testing and Administration

Utility

The compounds of the present invention are selective for and modulate the cardiac sarcomere, and are useful to bind to and/or potentiate the activity of cardiac myosin, increasing the rate at which myosin hydrolyzes ATP. As used in this context, "modulate" means either increasing or decreasing myosin activity, whereas "potentiate" means to increase activity. It has also been determined in testing representative compounds of the invention, that their administration can also increase the contractile force in cardiac muscle fiber.

The compounds, pharmaceutical formulations and methods of the invention are used to treat heart disease, including but not limited to: acute (or decompensated) congestive heart failure, and chronic congestive heart failure; particularly diseases associated with systolic heart dysfunction. Additional therapeutic utilities include administration to stabilize heart function in patients awaiting a heart transplant, and to assist a stopped or slowed heart in resuming normal function following use of a bypass pump.

Testing

ATP hydrolysis is employed by myosin in the sarcomere to produce force. Therefore, an increase in ATP hydrolysis would correspond to an increase in the force or velocity of muscle contraction. In the presence of actin, myosin ATPase activity is stimulated >100 fold. Thus, ATP hydrolysis not only measures myosin enzymatic activity but also its interaction with the actin filament. A compound that modulates the cardiac sarcomere can be identified by an increase or decrease in the rate of ATP hydrolysis by myosin, preferably exhibiting a 1.4 fold increase at concentrations less than 10 μM (more preferably, less than 1 μM). Preferred assays for such activity will employ myosin from a human source, although myosin from other organisms can also be used. Systems that model the regulatory role of calcium in myosin binding are also preferred.

Alternatively, a biochemically functional sarcomere preparation can be used to determine in vitro ATPase activity, for example, as described in U.S. Ser. No. 09/539,164, filed Mar. 29, 2000. The functional biochemical behavior of the sarcomere, including calcium sensitivity of ATPase hydrolysis, can be reconstituted by combining its purified individual components (particularly including its regulatory components and myosin). Another functional preparation is the in vitro motility assay. It can be performed by adding test compound to a myosin-bound slide and observing the velocity of actin filaments sliding over the myosin covered glass surface (Kron S J. (1991) Methods Enzymol. 196:399-416).

The in vitro rate of ATP hydrolysis correlates to myosin potentiating activity, which can be determined by monitoring the production of either ADP or phosphate, for example as described in Ser. No. 09/314,464, filed May 18, 1999. ADP production can also be monitored by coupling the ADP production to NADH oxidation (using the enzymes pyruvate kinase and lactate dehydrogenase) and monitoring the NADH level either by absorbance or fluorescence (Greengard, P., Nature 178 (Part 4534): 632-634 (1956); Mol Pharmacol 1970 January;6(1):31-40). Phosphate production can be monitored using purine nucleoside phosphorylase to couple phosphate production to the cleavage of a purine analog, which results in either a change in absorbance (Proc Natl Acad Sci USA 1992 Jun. 1;89(11):4884-7) or fluorescence (Biochem J 1990 Mar. 1;266(2):611-4). While a single measurement can be employed, it is preferred to take multiple measurements of the same sample at different times in order to determine the absolute rate of the protein activity; such measurements have higher specificity particularly in the presence of test compounds that have similar absorbance or fluorescence properties with those of the enzymatic readout.

Test compounds can be assayed in a highly parallel fashion using multiwell plates by placing the compounds either individually in wells or testing them in mixtures. Assay components including the target protein complex, coupling enzymes and substrates, and ATP can then be added to the wells and the absorbance or fluorescence of each well of the plate can be measured with a plate reader.

A preferred method uses a 384 well plate format and a 25 μL reaction volume. A pyruvate kinase/lactate dehydrogenase coupled enzyme system (Huang T G and Hackney D D. (1994) J Biol Chem 269(23):16493-16501) is used to measure the rate of ATP hydrolysis in each well. As will be appreciated, by those in the art, the assay components are added, in buffers and reagents. Since the methods outlined herein allow kinetic measurements, incubation periods are optimized to give adequate detection signals over the background. The assay is done in real time giving the kinetics of ATP hydrolysis, which increases the signal to noise ratio of the assay.

Modulation of cardiac muscle fiber contractile force can be measured using detergent permeabilized cardiac fibers (also referred to as skinned cardiac fibers), for example, as described by Haikala H, et al (1995) J Cardiovasc Pharmacol 25(5):794-801. Skinned cardiac fibers retain their intrinsic sarcomeric organization, but do not retain all aspects of cellular calcium cycling, this model offers two advantages: first, the cellular membrane is not a barrier to compound penetration, and second, calcium concentration is controlled. Therefore, any increase in contractile force is a direct measure of the test compound's effect on sarcomeric proteins. Tension measurements are made by mounting one end of the muscle fiber to a stationary post and the other end to a transducer that can measure force. After stretching the fiber to remove slack, the force transducer records increased tension as the fiber begins to contract. This measurement is called the isometric tension, since the fiber is not allowed to shorten. Activation of the permeabilized muscle fiber is accomplished by placing it in a buffered calcium solution, followed by addition of test compound or control. When tested in this manner, compounds of the invention caused an increase in force at calcium concentrations associated with physiologic contractile activity, but very little augmentation of force in relaxing buffer at low calcium concentrations or in the absence of calcium (the EGTA data point).

Selectivity for the cardiac sarcomere and cardiac myosin can be determined by substituting non-cardiac sarcomere components and myosin in one or more of the above-described assays and comparing the results obtained against those obtained using the cardiac equivalents.

A compound's ability to increase observed ATPase rate in an in vitro reconstituted sarcomere assay could result from the increased turnover rate of S1-myosin or, alternatively, increased sensitivity of a decorated actin filament to $Ca^{++}$-activation. To distinguish between these two possible modes of action, the effect of the compound on ATPase activity of S1 with undecorated actin filaments is initially measured. If an increase of activity is observed, the compound's effect on the Ca-responsive regulatory apparatus could be disproved. A second, more sensitive assay, can be employed to identify compounds whose activating effect on S1-myosin is enhanced in the presence of a decorated actin (compared to pure actin filaments). In this second assay activities of cardiac-S1 and skeletal-S1 on cardiac and skeletal regulated actin filaments (in all 4 permutations) are compared. A compound that displays its effect on cardiac-S1/cardiac actin and cardiac-S1/skeletal actin, but not on skeletal-S1/skeletal actin and skeletal-S1/cardiac actin systems, can be confidently classified as cardiac-S1 activator.

Initial evaluation of in vivo activity can be determined in cellular models of myocyte contractility, e.g., as described by Popping S, et al ((1996) Am. J. Physiol. 271: H357-H364) and Wolska B M, et al ((1996) Am. J. Physiol. 39:H24-H32). One advantage of the myocyte model is that the component systems that result in changes in contractility can be isolated and the major site(s) of action determined. Compounds with cellular activity (for example, selecting compounds having the following profile: >120% increase in fractional shortening over basal at 2 µM, limited changes in diastolic length (<5% change), and no significant decrease in contraction or relaxation velocities) can then be assessed in whole organ models, such as such as the Isolated Heart (Langendorff) model of cardiac function, in vivo using echocardiography or invasive hemodynamic measures, and in animal-based heart failure models, such as the Rat Left Coronary Artery Occlusion model. Ultimately, activity for treating heart disease is demonstrated in blinded, placebo-controlled, human clinical trials.

Administration

The compounds of Formula I are administered at a therapeutically effective dosage, e.g., a dosage sufficient to provide treatment for the disease states previously described. While human dosage levels have yet to be optimized for the compounds of the invention, generally, a daily dose is from about 0.05 to 100 mg/kg of body weight, preferably about 0.10 to 10.0 mg/kg of body weight, and most preferably about 0.15 to 1.0 mg/kg of body weight. Thus, for administration to a 70 kg person, the dosage range would be about 3.5 to 7000 mg per day, preferably about 7.0 to 700.0 mg per day, and most preferably about 10.0 to 100.0 mg per day. The amount of active compound administered will, of course, be dependent on the subject and disease state being treated, the severity of the affliction, the manner and schedule of administration and the judgment of the prescribing physician; for example, a likely dose range for oral administration would be about 70 to 700 mg per day, whereas for intravenous administration a likely dose range would be about 700 to 7000 mg per day, the active agents being selected for longer or shorter plasma half-lives, respectively.

Administration of the compounds of the invention or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administration are customary in treating the indications that are the subject of the present invention.

Pharmaceutically acceptable compositions include solid, semi-solid, liquid and aerosol dosage forms, such as, e.g., tablets, capsules, powders, liquids, suspensions, suppositories, aerosols or the like. The compounds can also be administered in sustained or controlled release dosage forms, including depot injections, osmotic pumps, pills, transdermal (including electrotransport) patches, and the like, for prolonged and/or timed, pulsed administration at a predetermined rate. Preferably, the compositions are provided in unit dosage forms suitable for single administration of a precise dose.

The compounds can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical formulation will contain about 0.005% to 95%, preferably about 0.5% to 50% by weight of a compound of the invention. Actual methods of preparing such dosage forms are known, or will be apparent, to those skilled in this art; for example, see *Remington's Pharmaceutical Sciences*, Mack Publishing Company, Easton, Pa.

In addition, the compounds of the invention can be co-administered with, and the pharmaceutical compositions can include, other medicinal agents, pharmaceutical agents, adjuvants, and the like. Suitable additional active agents include, for example: therapies that retard the progression of heart failure by down-regulating neurohormonal stimulation of the heart and attempt to prevent cardiac remodeling (e.g., ACE inhibitors or p-blockers); therapies that improve cardiac function by stimulating cardiac contractility (e.g., positive inotropic agents, such as the β-adrenergic agonist dobutamine or the phosphodiesterase inhibitor milrinone); and therapies that reduce cardiac preload (e.g., diuretics, such as furosemide).

In one preferred embodiment, the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule.

Liquid pharmaceutically administrable compositions can, for example, be prepared by dissolving, dispersing, etc. an active compound as defined above and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid which will be subsequently diluted to the above percentages. Preferably the composition will comprise 0.2-2% of the active agent in solution.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, preferably less than 10 microns.

Use in Screening

Generally, to employ the compounds of the invention in a method of screening for myosin binding, myosin is bound to a support and a compound of the invention is added to the assay. Alternatively, the compound of the invention can be bound to the support and the myosin added. Classes of compounds among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like. See, e.g., U.S. Pat. No. 6,495,337, incorporated herein by reference.

EXAMPLES

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

Example 1

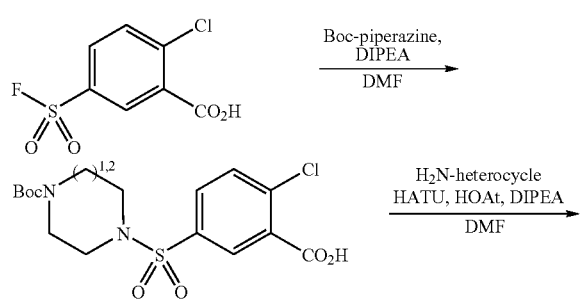

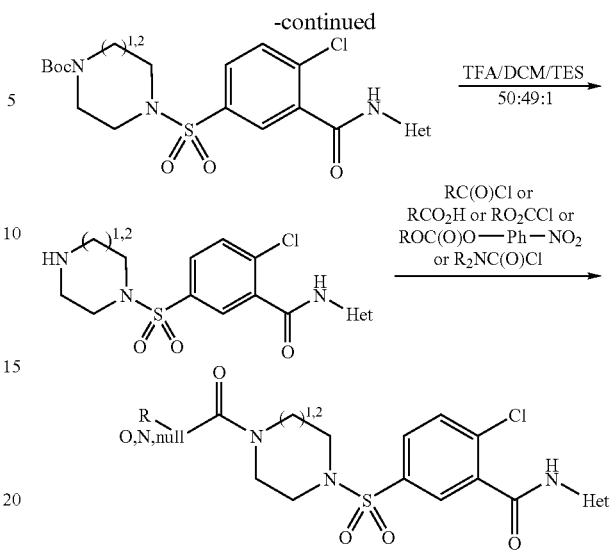

Preparation of 4-(3-Carboxy-4-chloro-benzenesulfonyl)-piperazine-1-carboxylic acid ethyl ester 2-Chloro-5-fluorosulfonylbenzoic acid (Acros Organics, 105 mg, 440 μmol, 1.0 eq) was placed in a vial and the vial was flushed with nitrogen and a positive pressure was maintained. Anhydrous dichloromethane (1.4 mL) was added, followed by ethyl 1-piperazine carboxylate (80 μL, 528 μmol, 1.2 eq) and ethyldiisopropylamine (redistilled, 80 μL, 440 μmol, 1.0 eq). The mixture was stirred for 1.5 h after which time additional piperazine was added (60 μL, 352 μmol, 0.8 eq). After 14 h the mixture was analyzed by reverse-phase HPLC-MS in negative ionization mode. The sulfonyl fluoride starting material was present, as well as a less polar compound showing (M–1) ion in about 35:65 ratio. An additional 0.35 eq of piperazine and ethyldiisopropylamine each (154 μmol, 30 μl) were added and the mixture was stirred for 4 h. HPLC-MS at this time indicated little progress and an additional 0.25 eq of piperazine (100 mmol, 20 μL) was added. After stirring for 14 h HPLC-MS indicated the reaction was complete. The reaction mixture was diluted with 2 mL of ethyl acetate, washed with 1 M HCl solution (2×1 mL) and dried over anhydrous sodium sulfate. The solution was filtered, the solvents removed on a rotary evaporator and vacuum pump to afford 134 mg of a white solid, 81%. NOTE: Addition of excess nucleophilic amine at the beginning of the reaction results in significant bis addition, giving sulfonamide and carboxamide product. Stepwise addition of nucleophilic amine as needed suppresses formation of this side product.

Preparation of 4-[4-Chloro-3-(5-phenyl-[1,3,4]thiadiazol-2-ylcarbamoyl)-benzenesulfonyl]-piperazine-1-carboxylic acid ethyl ester The benzoic acid piperazine ethyl ester from above (131 mg, 348 μmol, 1.0 eq) was placed in a vial along with 2-amino-5-phenyl-1,3,4-thiadiazole sulfate (115 mg, 417 μmol, 1.2 eq), HBTU (Advanced Chem Tech, 198 mg, 521 μmol, 1.5 eq) and HOBt hydrate (80 mg, 521 μmol, 1.5 eq). The vial was flushed with nitrogen and a positive pressure was maintained. Anhydrous dimethylformamide (1.7 mL) was added, followed by ethyldiisopropylamine (redistilled, 120 μL, 695 μmol, 2.0 eq) and the mixture was stirred for 14 h.

Analysis by reverse-phase HPLC-MS in positive mode indicated that the acid starting material had been consumed and replaced with a much less polar compound showing the desired (M+1). The reaction mixture was diluted with 4 mL of water, the resulting precipitate was collected by filtration and washed with the following: water×2, 1 M HCl solution×2, saturated sodium bicarbonate solution×2, water×2 and hexanes×1 and dried under suction. 119 mg of an off-white solid was obtained, 64% yield.

Example 2

Preparation of 4-(3-Carboxy-4-chloro-benzenesulfonyl)-piperazine-1-carboxylic acid tert-butyl ester Prepared as for the compound above with these modifications: after the addition of 2.0 eq total of tert-butyl 1-piperazine carboxylate on day 1, HPLC-MS analysis showed the reaction to be only ⅓ complete. An additional 1.4 eq of piperazine was added and the reaction was stirred for 24 h. After this time the reaction was found to be complete and the workup was performed as for the ethyl case. Instead of washing with 1 M HCl solution, 0.3M potassium hydrogen sulfate solution was used and a wash with saturated sodium chloride solution was also added prior to drying and concentrating. A quantitative yield of desired product was obtained.

Preparation of 4-[4-Chloro-3-(1H-imidazol-2-ylcarbamoyl)-benzenesulfonyl]-piperazine-1-carboxylic acid tert-butyl ester The benzoic acid piperazine tert-butyl ester from above (1.57 g, 3.88 mmol, 1.0 eq) was placed in a 100 mL round-bottom flask along with 2-aminoimidazole sulfate (Aldrich, 615 mg, 4.65 mmol, 1.2 eq), HATU (PE Biosystems, 2.21 g, 5.82 mmol, 1.5 eq) and HOAt (Avocado, 792 mg, 5.82 mmol, 1.5 eq). The flask was capped with a septum, flushed with nitrogen and a positive pressure was maintained. Anhydrous dimethylformamide (17 mL) was added, followed by ethyldiisopropylamine (redistilled, 1.4 mL, 7.76 mmol, 2.0 eq) and the mixture was stirred for 14-h. Analysis by reverse-phase HPLC-MS in positive mode indicated that the acid starting material had been consumed and replaced with a much less polar compound showing the desired (M+1). The reaction mixture was diluted with 80 mL of water, the resulting precipitate was collected by filtration and washed with the following: water×3, hexanes×2 and dried under suction to afford 1.46 g of an off-white solid. The crude material was purified (silica gel flash column, 5.1 cm×15 cm) eluting with EtOAc-hexanes-triethylamine (89:10:1 v/v) then EtOAc to provide 896 mg off-white solid, 49% yield. TLC EtOAc-triethylamine (99:1 v/v) $R_f$ 0.27.

Preparation of 2-Chloro-5-[4-(2-cyclohexyl-acetyl)-piperazine-1-sulfonyl]-N-(1H-imidazol-2-yl)-benzamide The Boc-piperazine imidazole compound from above (109 mg, 232 mol, 1.0 eq) was placed in a vial and treated with 2.6 mL of 50:49:1 trifluoroacetic acid/dichloromethane/triethylsilane. After 15 min Boc removal was complete as evidenced by reverse-phase HPLC-MS, and the solvents were removed in vacuo. The residue was azeotroped 3×chloroform and placed under vacuum for 1 h. 1-ethyl-(3-dimethylaminopropyl)carbodiimide HCl (EDC) (Advanced Chem Tech, 67 mg, 348 μmol, 1.5 eq), HOBt hydrate (57 mg, 371 μmol, 1.6 eq) were added to the vial, the vial was capped, flushed with nitrogen and a positive pressure was maintained. Anhydrous dichloromethane (1.7 mL) was added, followed by ethyldiisopropylamine (redistilled, 250 μL, 1.39 mmol, 6.0 eq) and cyclohexylacetic acid (TCl, 40 μL, 278 μmol, 1.2 eq) and the mixture was stirred for 14 h. Analysis by reverse-phase HPLC-MS in positive mode indicated that the piperazine starting material had been consumed and replaced with a much less polar compound showing the desired (M+1). The reaction mixture was diluted with 4 mL of EtOAc, and the organic layer was washed with 2 mL each of the following: water×3, saturated sodium bicarbonate solution×1, saturated sodium chloride×1. The organic extracts were dried over anhydrous sodium sulfate, filtered and concentrated to afford 61 mg of an off-white solid, 78% yield.

Preparation of 4-[4-Chloro-3-(1H-imidazol-2-ylcarbamoyl)-benzenesulfonyl]-piperazine-1-carboxylic acid (R)-sec-butyl ester The Boc-piperazine imidazole compound from above (148 mg, 315 μmol, 1.0 eq) was placed in a vial and treated with 3.6 mL of 50:49:1 trifluoroacetic acid/dichloromethane/triethylsilane as described above for the cyclohexyl acetamide compound. (R)-Carbonic acid sec-butyl ester 4-nitro-phenyl ester, 93% wt. (89 mg, 346 μmol, 1.1 eq) and 3 mg DMAP were added to the vial, the vial was capped, flushed with nitrogen and a positive pressure was maintained. Anhydrous DMF (2.1 mL) was added, followed by ethyldiisopropylamine (redistilled, 170 μL, 945 μmol, 3.0 eq) and the mixture was stirred for 14 h at 40° C. Analysis by reverse-phase HPLC-MS in positive mode indicated that the very polar unprotected piperazine starting material had been consumed and replaced with a much less polar compound showing the desired (M+1), as well as a small amount of even less polar bis-acylated material. The heat was removed and the reaction mixture was diluted with 4 mL of 2N NaOH solution and stirred for 10 min. The mixture was extracted with EtOAc (3×2 mL), and the organic layer was washed with 2 mL each of the following: 2N NaOH×5 (until yellow color disappeared), water×1, 10% HOAc solution×1, water×1, saturated sodium bicarbonate solution×1, saturated sodium chloride×1. The organic extracts were dried over anhydrous sodium sulfate, filtered and concentrated to afford 121 mg of an off-white solid, 82% yield.

Preparation of 4-[4-Chloro-3-(1H-imidazol-2-ylcarbamoyl)-benzenesulfonyl]-piperazine-1-carboxylic acid iso-propyl ester The Boc-piperazine imidazole compound from above (86 mg, 183 μmol, 1.0 eq) was placed in a vial and treated with 1.8 mL of 50:49:1 trifluoroacetic acid/dichloromethane/triethylsilane as described above for the cyclohexyl acetamide compound. DMAP (2 mg) were added to the vial, the vial was capped, flushed with nitrogen and a positive pressure was maintained. Anhydrous DCM (2.1 mL) was added, followed by ethyldiisopropylamine (redistilled, 120 μL, 640 μmol, 3.5 eq) and a 1.0 M solution of isopropyl chloroformate in toluene (220 μL, 220 μmol, 1.2 eq) and the mixture was stirred for 14 h. Analysis by reverse-phase HPLC-MS in positive mode indicated that the very polar unprotected piperazine starting material had been consumed and replaced with a much less polar compound showing the desired (M+1). A solid had precipitated. The solvent was removed in vacuo and the solid was taken up in 1 mL of DMF and re-precipitated with 4 mL of water, isolated by filtration and washed with: water×3, hexanes×2 and dried under suction. A white solid was obtained, 50 mg (60% yield).

Example 3

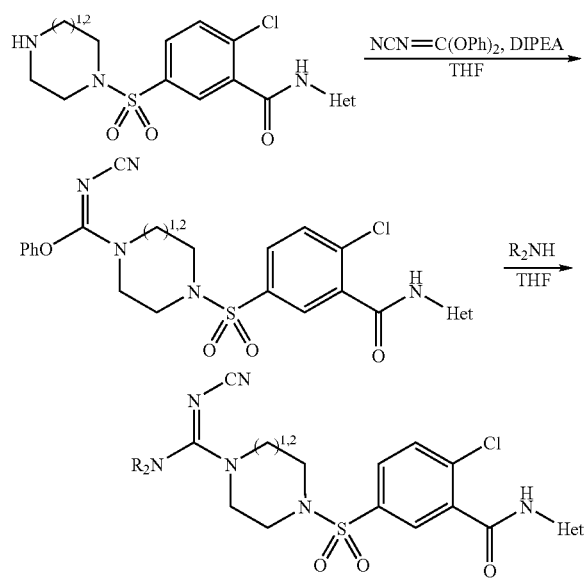

Preparation of 4-[4-Chloro-3-(1H-imidazol-2-ylcarbamoyl)-benzenesulfonyl]-N-cyano-piperazine-1-carboximidic acid phenyl ester The Boc-piperazine imidazole compound from above (2.04 g, 4.33 mmol, 1.0 eq) was treated with 50:49:1 trifluoroacetic acid/dichloromethane/triethylsilane as described above for the cyclohexyl acetamide compound. The residue was treated with saturated sodium bicarbonate solution until pH>8, then the solution was extracted with EtOAc and concentrated in vacuo to afford 1.6 g free amine. Diphenylcyanocarbonimidate (1.08 g, 4.54 mmol, 10.5 eq) was added to the flask and it was capped, flushed with nitrogen and a positive pressure was maintained. Anhydrous THF (30 mL) was added, followed by ethyldiisopropylamine (redistilled, 830 µL, 4.76 mmol, 1.1 eq) and the mixture was stirred for 1 h. Analysis by reverse-phase HPLC-MS in positive mode indicated that the very polar unprotected piperazine starting material had been consumed and replaced with a compound showing the desired (M+1). The solvents were removed in vacuo.

Preparation of 2-Chloro-5-[4-(N-cyclopentyl-N'-cyano-carbamimidoyl)-piperazine-1-sulfonyl]-N-(1H-imidazol-2-yl)-benzamide The phenyl imidate from above (100 mg, 195 µmol, 1.0 eq) was placed in a vial which was capped, flushed with nitrogen and a positive pressure was maintained. Anhydrous THF (5 mL) was added, followed by cyclopentylamine (100 µL, 973 µmol, 5.0 eq) and the mixture was stirred for 48 h after which the solvent was removed in vacuo. The residue was purified by reverse-phase HPLC to afford 27 mg product, 27% yield.

Example 4

Preparation of 2-Chloro-5-(4-methyl-piperazine-1-sulfonyl)-benzoic acid

2-Chloro-5-fluorosulfonylbenzoic acid (Acros Organics, 195 mg, 813 µmol, 1.0 eq) was placed in a vial and the vial was flushed with nitrogen and a positive pressure was maintained. Anhydrous dichloromethane (2.7 mL) was added, followed by 1-methylpiperazine (110 µL, 976 µmol, 1.2 eq). The mixture was stirred for 2 h after which time an additional 1.2 eq was added. After 14 h the mixture was analyzed by reverse-phase HPLC-MS in positive ionization mode. The less polar sulfonyl fluoride starting material was gone and replaced with a very polar compound with the desired (M+1). The solvents were removed in vacuo to afford 407 mg of a pale yellow solid. By $^1$H-NMR the desired compound was present, contaminated with methylpiperazine.

Preparation of 2-Chloro-5-(4-methyl-piperazine-1-sulfonyl)-benzoic acid methyl ester The crude methylpiperazine benzoic acid from above (259 mg, 813 µmol, 1.0 eq) was dissolved in 4 mL of 30% MeOH in benzene. 2.0 M Trimethylsilyl diazomethane in hexanes solution (410 µL, 813 µmol, 1.0 eq) was added dropwise. After 15 min the mixture was analyzed by reverse-phase HPLC-MS in positive mode. Starting material was present, as well as less polar product. Another 1.0 eq of diazomethane compound was added and the reaction was monitored again after 15 min. An additional 0.2 eq of diazomethane was added (90 µL, 178 µmol) and after 15 min the reaction was judged to be complete by HPLC-MS. A few drops glacial HOAc were added until the yellow color disappeared and the solvents were removed in vacuo to afford 491 mg of a yellow glass. This was taken up in 2 mL 50%-saturated sodium bicarbonate solution (pH>0.8) and extracted with dichloromethane (3×1 mL). The extracts were dried over anhydrous sodium sulfate, filtered and concentrated to afford 224 mg of yellow oil, 83%.

Preparation of Lithium 2-chloro-5-(4-methyl-piperazine-1-sulfonyl)-benzoate

The methylpiperazine methyl ester from above (197 mg, 592 µmol, 1.0 eq) was placed in a vial, dissolved in 1.5 mL of MeOH and 30 µL of water. LiOH hydrate (26 mg, 622 µmol, 1.05 eq) was added and the vial was capped, flushed with nitrogen and a positive pressure was maintained. The mixture was heated at 60° C. for 4 h at which time it was judged to be complete by reverse-phase HPLC-MS. The solvents were removed in vacuo to afford 197 mg of a white solid.

Preparation of 2-Chloro-5-(4-methyl-piperazine-1-sulfonyl)-N-(5-phenyl-[1,3,4]thiadiazol-2-yl)-benzamide The methylpiperazine acid salt from above (93 mg, 286 µmol, 1.0 eq) was coupled with 2-amino-5-phenyl-1,3,4-thiadiazole sulfate using the HBTU protocol as described above, except that the ethyldiisopropylamine was added 1 h after the reaction was started in order to neutralize the acid salt and effect dissolution. After 3 h total the reaction was complete by reverse-phase HPLC-MS analysis in positive mode. The reaction mixture was diluted with 3 mL of water and taken to pH=8 by addition of saturated bicarbonate solution. The resulting precipitate was collected by filtration and washed with the following: water×2 and hexanes×1. The product was isolated as 109 mg of an off-white solid, 80% yield.

Example 5

Synthesis of Starting Materials

2-Amino-4-phenylimidazole, a reagent in the synthesis of compounds of Formula I, was synthesized from the procedure of: Little, T. L.; Webber, S. E. "A Simple and Practical Synthesis of 2-Aminoimidazoles" *J. Org. Chem.* 1994, 59, 7299-7305, which is incorporated herein by reference.

2-Amino-5-phenylpyrimidine was synthesized in an analogous fashion to the procedure described in: Gong, Y.; Pauls, H. W. "A Convenient Synthesis of Heteroarylbenzoic Acids via Suzuki Reaction" *Synlett*, 2000, 6, 829-831, which is incorporated herein by reference.

2-Aminooxazole was prepared from the procedure of: Cockerill, A. F.; Deacon, A.; Harrison, R. G.; Osborne, D. J.; Prime, D. M.; Ross, W. J.; Todd, A.; Verge, J. P. "An Improved Synthesis of 2-Amino-1,3-Oxazoles Under Basic Conditions" *Synthesis*, 1976, 591-593, which is incorporated herein by reference.

2-Amino-4-methylimidazole was prepared according to the procedure described in: Little, T. L.; Webber, S. E. "A Simple and Practical Synthesis of 2-Aminoimidazoles" *J. Org. Chem.* 1994, 59, 7299-7305, which is incorporated herein by reference.

Example 6

Preparation of (R)-Carbonic acid sec-butyl ester 4-nitro-phenyl ester

4-Nitrophenyl chloroformate (1.91 g, 9.50 mmol, 1.1 eq) was placed in a vial and the vial was flushed with nitrogen and a positive pressure was maintained. Anhydrous dichloromethane (10 mL) was added, followed by (R)-sec-butyl alcohol (Acros Organics, 800 µL, 8.63 mmol, 1.0 eq) and anhydrous pyridine (770 µL, 9.50 mmol, 1.1 eq). After 15 h one nonpolar compound was observed by HPLC-MS but which did not ionize in either positive or negative mode. The reaction mixture was diluted with 10 mL of ethyl acetate, washed with 7 mL each of the following: 0.5 M NaOH solution×2, water×1, 1 M HCl solution×1, water×1, saturated sodium chloride×1 and dried over anhydrous sodium sulfate. The solution was filtered, the solvents removed on a rotary evaporator and vacuum pump to afford 2.11 g of a pale yellow solid. This was shown to contain 11 mol % 4-nitrophenol by $^1$H-NMR and was judged to be 93% pure by weight. Total yield was therefore 95%.

Example 7

Target Identification Assays

Specificity assays: Compound specificity towards cardiac myosin is evaluated by comparing the effect of the compound on actin-stimulated ATPase of a panel of myosin isoforms: cardiac, skeletal and smooth muscle, at a single 50 µM compound concentration.

Myofibril assays: To evaluate the effect of compounds on the ATPase activity of full-length cardiac myosin in the context of native sarcomere, skinned myofibril assays are performed. Rat cardiac myofibrils are obtained by homogenizing rat cardiac tissue in the presence of detergent. Such treatment removes membranes and majority of soluble cytoplasmic proteins but leaves intact cardiac sarcomeric acto-myosin apparatus. Myofibril preparations retain the ability to hydrolyze ATP in an $Ca^{++}$ controlled manner. ATPase activities of such myofibril preparations in the presence and absence of compounds are assayed at $Ca^{++}$ concentrations giving 50% and 100% of a maximal rate.

Example 8

In Vitro Model of Dose Dependent Cardiac Myosin ATPase Modulation

Dose responses are measured using a calcium-buffered, pyruvate kinase and lactate dehydrogenase-coupled ATPase assay containing the following reagents (concentrations expressed are final assay concentrations): Potassium PIPES (12 mM), $MgCl_2$ (2 mM), ATP (1 mM), DTT (1 mM), BSA (0.1 mg/ml), NADH (0.5 mM), PEP (1.5 mM), pyruvate kinase (4 U/ml), lactate dehydrogenase (8 U/ml), and antifoam (90 ppm). The pH is adjusted to 6.80 at 22° C. by addition of potassium hydroxide. Calcium levels are controlled by a buffering system containing 0.6 mM EGTA and varying concentrations of calcium, to achieve a free calcium concentration of $1\times10^{-4}$ M to $1\times10^{-8}$ M.

The protein components specific to this assay are bovine cardiac myosin subfragment-1 (typically 0.5 µM), bovine cardiac actin (14 µM), bovine cardiac tropomyosin (typically 3 µM), and bovine cardiac troponin (typically 3-8 µM). The exact concentrations of tropomyosin and troponin are determined empirically, by titration to achieve maximal difference in ATPase activity when measured in the presence of 1 mM EGTA versus that measured in the presence of 0.2 mM $CaCl_2$. The exact concentration of myosin in the assay is also determined empirically, by titration to achieve a desired rate of ATP hydrolysis. This varies between protein preparations, due to variations in the fraction of active molecules in each preparation.

Compound dose responses are typically measured at the calcium concentration corresponding to 50% of maximal ATPase activity ($pCa_{50}$), so a preliminary experiment is performed to test the response of the ATPase activity to free calcium concentrations in the range of $1\times10^{-4}$ M to $1\times10^{-8}$ M. Subsequently, the assay mixture is adjusted to the $pCa_{50}$ (typically $3\times10^{-7}$ M). Assays are performed by first preparing a dilution series of test compound, each with an assay mixture containing potassium Pipes, $MgCl_2$, BSA, DTT, pyruvate kinase, lactate dehydrogenase, myosin subfragment-1, antifoam, EGTA, $CaCl_2$, and water. The assay is started by adding an equal volume of solution containing potassium Pipes, $MgCl_2$, BSA, DTT, ATP, NADH, PEP, actin, tropomyosin, troponin, antifoam, and water. ATP hydrolysis is monitored by absorbance at 340 nm. The resulting dose response curve is fit by the 4 parameter equation y=Bottom+((Top-Bottom)/(1+((EC50/X)^Hill))). The AC1.4 is defined as the concentration at which ATPase activity is 1.4-fold higher than the bottom of the dose curve.

Example 9

Myocyte Assays

PREPARATION OF ADULT CARDIAC VENTRICULAR RAT MYOCYTES. Adult male Sprague-Dawley rats are anesthetized with a mixture of isoflurane gas and oxygen. Hearts are quickly excised, rinsed and the ascending aorta cannulated. Continuous retrograde perfusion is initiated on the hearts at a perfusion pressure of 60 cm $H_2O$. Hearts are first perfused with a nominally Ca²⁺ free modified Krebs solution of the following composition: 110 mM NaCl, 2.6 mM KCL, 1.2 mM $KH_2PO_4 7H_2O$, 1.2 mM $MgSO_4$, 2.1 mM $NaHCO_3$, 11 mM glucose and 4 mM Hepes (all Sigma). This medium is not recirculated and is continually gassed with $O_2$. After approximately 3 minutes the heart is perfused with modified Krebs buffer supplemented with 3.3% collagenase (169 p/mg activity, Class II, Worthington Biochemical Corp., Freehold, N.J.) and 25 µM final calcium concentration until the heart becomes sufficiently blanched and soft. The heart is removed from the cannulae, the atria and vessels discarded and the ventricles are cut into small pieces. The myocytes are dispersed by gentle agitation of the ventricular tissue in fresh collagenase containing Krebs prior to being gently forced through a 200 µm nylon mesh in a 50 cc tube. The resulting myocytes are resuspended in modified Krebs solution containing 25 µm calcium. Myocytes are made calcium tolerant by addition of a calcium solution (100 mM stock) at 10 minute intervals until 100 µM calcium is achieved. After 30 minutes the supernatant is discarded and 30-50 ml of Tyrode buffer (137 mM NaCL, 3.7 mM KCL, 0.5 mM MgCL, 11 mM glucose, 4 mM Hepes, and 1.2 mM $CaCl_2$, pH 7.4) is added to cells. Cells are kept for 60 min at 37° C. prior to initiating experiments and used within 5 hrs of isolation. Preparations of cells are used only if cells first passed QC criteria by responding to a standard (>150% of basal) and isoproterenol (ISO; >250% of basal). Additionally, only cells whose basal contractility is between 3 and 8% are used in the following experiments.

ADULT VENTRICULAR MYOCYTE CONTRACTILITY EXPERIMENTS. Aliquots of Tyrode buffer containing myocytes are placed in perfusion chambers (series 20 RC-27NE; Warner Instruments) complete with heating platforms. Myocytes are allowed to attach, the chambers heated to 37° C., and the cells then perfused with 37° C. Tyrode buffer. Myocytes are field stimulated at 1 Hz in with platinum electrodes (20% above threshold). Only cells that have clear striations, and are quiescent prior to pacing are used for contractility experiments. To determine basal contractility, myocytes are imaged through a 40× objective and using a variable frame rate (60-240 Hz) charge-coupled device camera, the images are digitized and displayed on a computer screen at a sampling speed of 240 Hz. [Frame grabber, myopacer, acquisition, and analysis software for cell contractility are available from IonOptix (Milton, Mass.).] After a minimum 5 minute basal contractility period, test compounds (0.01-15 µM) are perfused on the myocytes for 5 minutes. After this time, fresh Tyrode buffer is perfused to determine compound washout characteristics. Using edge detection strategy, contractility of the myocytes and contraction and relaxation velocities are continuously recorded.

CONTRACTILITY ANALYSIS: Three or more individual myocytes are tested per compound, using two or more different myocyte preparations. For each cell, twenty or more contractility transients at basal (defined as 1 min prior to compound infusion) and after compound addition, are averaged and compared. These average transients are analyzed to determine changes in diastolic length, and using the Ionwizard analysis program (IonOptix), fractional shortening (% decrease in the diastolic length), and maximum contraction and relaxation velocities (um/sec) are determined. Analysis of individual cells are combined. Increase in fractional shortening over basal indicates potentiation of myocyte contractility.

CALCIUM TRANSIENT ANALYSIS: Fura loading: Cell permeable Fura-2 (Molecular Probes) is dissolved in equal amounts of pluronic (Mol Probes) and FBS for 10 min at RT. A 1 µM Fura stock solution is made in Tyrode buffer containing 500 mM probenecid (Sigma). To load cells, this solution is added to myocytes at RT. After 10 min. the buffer is removed, the cells washed with Tyrode containing probenecid and incubated at RT for 10 min. This wash and incubation is repeated. Simultaneous contractility and calcium measurements are determined within 40 min. of loading.

Imaging: A test compound is perfused on cells. Simultaneous contractility and calcium transient ratios are determined at baseline and after compound addition. Cells are digitally imaged and contractility determined as described above, using that a red filter in the light path to avoid interference with fluorescent calcium measurements. Acquisition, analysis software and hardware for calcium transient analysis are obtained from IonOptix. The instrumentation for fluorescence measurement includes a xenon arc lamp and a Hyperswitch dual excitation light source that alternates between 340 and 380 wavelengths at 100 Hz by a galvo-driven mirror. A liquid filled light guide delivers the dual excitation light to the microscope and the emission fluorescence is determined using a photomultiplier tube (PMT). The fluorescence system interface routes the PMT signal and the ratios are recorded using the IonWizard acquisition program.

Analysis: For each cell, ten or more contractility and calcium ratio transients at basal and after compound addition, where averaged and compared. Contractility average transients are analyzed using the Ionwizard analysis program to determine changes in diastolic length, and fractional shortening (% decrease in the diastolic length). The averaged calcium ratio transients are analyzed using the Ionwizard analysis program to determine changes in diastolic and systolic ratios and the 75% time to baseline ($T_{75}$).

DURABILITY: To determine the durability of response, myocytes are challenged with a test compound for 25 minutes followed by a 2 min. washout period. Contractility response is compared at 5 and 25 min. following compound infusion.

THRESHOLD POTENTIAL: Myocytes are field stimulated at a voltage approximately 20% above threshold. In these experiments the threshold voltage (minimum voltage to pace cell) is empirically determined, the cell paced at that threshold and then the test compound is infused. After the compound activity is at steady state, the voltage is decreased for 20 seconds and then restarted. Alteration of ion channels corresponds to increasing or lowering the threshold action potential.

HZ FREQUENCY: Contractility of myocytes is determined at 3 Hz as follows: a 1 min. basal time point followed by perfusion of the test compound for 5 min. followed by a 2 min. washout. After the cell contractility has returned completely to baseline the Hz frequency is decreased to 1. After an initial acclimation period the cell is challenged by the same compound. As this species, rat, exhibits a negative force frequency at 1 Hz, at 3 Hz the FS of the cell should be lower, but the cell should still respond by increasing its fractional shortening in the presence of the compound.

ADDITIVE WITH ISOPROTERENOL: To demonstrate that a compound act via a different mechanism than the adrenergic stimulant isoproterenol, cells are loaded with fura-2 and simultaneous measurement of contractility and calcium ratios are determined. The myocytes are sequentially challenged with 5 µm a test compound, buffer, 2 nM isoproterenol, buffer, and a combination of a test compound and isoproterenol.

Example 10

In vitro Model of Dose Dependent Cardiac Myosin ATPase Modulation

Bovine and rat cardiac myosins are purified from the respective cardiac tissues. Skeletal and smooth muscle myosins used in the specificity studies are purified from rabbit skeletal muscle and chicken gizzards, respectively. All myosins used in the assays are converted to a single-headed soluble form (S1) by a limited proteolysis with chymotrypsin. Other sarcomeric components: troponin complex, tropomyosin and actin are purified from bovine hearts (cardiac sarcomere) or chicken pectoral muscle (skeletal sarcomere).

Activity of myosins is monitored by measuring the rates of hydrolysis of ATP. Myosin ATPase is very significantly activated by actin filaments. ATP turnover is detected in a coupled enzymatic assay using pyruvate kinase (PK) and lactate dehydrogenase (LDH). In this assay each ADP produced as a result of ATP-hydrolysis is recycled to ATP by PK with a simultaneous oxidation of NADH molecule by LDH. NADH oxidation can be conveniently monitored by decrease in absorbance at 340 nm wavelength.

Dose responses are measured using a calcium-buffered, pyruvate kinase and lactate dehydrogenase-coupled ATPase assay containing the following reagents (concentrations expressed are final assay concentrations): Potassium PIPES (12 mM), MgCl$_2$ (2 mM), ATP (1 mM), DTT (1 mM), BSA (0.1 mg/ml), NADH (0.5 mM), PEP (1.5 mM), pyruvate kinase (4 U/ml), lactate dehydrogenase (8 U/ml), and antifoam (90 ppm). The pH is adjusted to 6.80 at 22° C. by addition of potassium hydroxide. Calcium levels are controlled by a buffering system containing 0.6 mM EGTA and varying concentrations of calcium, to achieve a free calcium concentration of $1\times10^{-4}$ M to $1\times10^{-8}$ M.

The protein components specific to this assay are bovine cardiac myosin subfragment-1 (typically 0.5 μM), bovine cardiac actin (14 μM), bovine cardiac tropomyosin (typically 3 μM), and bovine cardiac troponin (typically 3-8 μM). The exact concentrations of tropomyosin and troponin are determined empirically, by titration to achieve maximal difference in ATPase activity when measured in the presence of 1 mM EGTA versus that measured in the presence of 0.2 mM CaCl$_2$. The exact concentration of myosin in the assay is also determined empirically, by titration to achieve a desired rate of ATP hydrolysis. This varies between protein preparations, due to variations in the fraction of active molecules in each preparation.

Compound dose responses are typically measured at the calcium concentration corresponding to 50% of maximal ATPase activity (pCa$_{50}$), so a preliminary experiment is performed to test the response of the ATPase activity to free calcium concentrations in the range of $1\times10^{-4}$ M to $1\times10^{-8}$ M. Subsequently, the assay mixture is adjusted to the pCa$_{50}$ (typically $3\times10^{-7}$ M). Assays are performed by first preparing a dilution series of test compound, each with an assay mixture containing potassium Pipes, MgCl$_2$, BSA, DTT, pyruvate kinase, lactate dehydrogenase, myosin subfragment-1, antifoam, EGTA, CaCl$_2$, and water. The assay is started by adding an equal volume of solution containing potassium Pipes, MgCl$_2$, BSA, DTT, ATP, NADH, PEP, actin, tropomyosin, troponin, antifoam, and water. ATP hydrolysis is monitored by absorbance at 340 nm. The resulting dose response curve is fit by the 4 parameter equation y=Bottom+((Top-Bottom)/(1+((EC50/X)^Hill))). The AC1.4 is defined as the concentration at which ATPase activity is 1.4-fold higher than the bottom of the dose curve.

Ability of a compound to activate cardiac myosin is evaluated by the effect of the compound on the actin stimulated ATPase of S1 subfragment. Actin filaments in the assay are decorated with troponin and tropomyosin and Ca$^{++}$ concentration is adjusted to a value that would result in 50% of maximal activation. S1 ATPase is measured in the presence of a dilution series of the compound. Compound concentration required for 40% activation above the ATPase rate measured in the presence of control (equivalent volume of DMSO) is reported as AC$_{40}$.

Example 11

In vivo Fractional Shortening Assay

ANIMALS Male Sprague Dawley rats from Charles River Laboratories (275-350 g) are used for bolus efficacy and infusion studies. Heart failure animals are described below. They are housed two per cage and have access to food and water ad libitum. There is a minimum three-day acclimation period prior to experiments.

ECHOCARDIOGRAPHY Animals are anesthetized with isoflurane and maintained within a surgical plane throughout the procedure. Core body temperature is maintained at 37° C. by using a heating pad. Once anesthetized; animals are shaven and hair remover is applied to remove all traces of fur from the chest area. The chest area is further prepped with 70% ETOH and ultrasound gel is applied. Using a GE System Vingmed ultrasound system (General Electric Medical Systems), a 10 MHz probe is placed on the chest wall and images are acquired in the short axis view at the level of the papillary muscles. 2-D M-mode images of the left ventricle are taken prior to, and after, compound bolus injection or infusion. In vivo fractional shortening ((end diastolic diameter–end systolic diameter)/end diastolic diameter×100) is determined by analysis of the M-mode images using the GE EchoPak software program.

BOLUS AND INFUSION EFFICACY For bolus and infusion protocols, fractional shortening is determined using echocardiography as described above. For bolus and infusion protocols, five pre-dose M-Mode images are taken at 30 second intervals prior to bolus injection or infusion of compounds. After injection, M-mode images are taken at 1 min and at five minute intervals thereafter up to 30 min. Bolus injection (0.5-5 mg/kg) or infusion is via a tail vein catheter. Infusion parameters are determined from pharmacokinetic profiles of the compounds. For infusion, animals received a 1 minute loading dose immediately followed by a 29 minute infusion dose via a tail vein catheter. The loading dose is calculated by determining the target concentration×the steady state volume of distribution. The maintenance dose concentration is determined by taking the target concentration×the clearance. Compounds are formulated in 25% cavitron vehicle for bolus and infusion protocols. Blood samples are taken to determine the plasma concentration of the compounds.

Example 12

Hemodynamics in Normal and Heart Failure Animals

Animals are anesthetized with isoflurane, maintained within a surgical plane, and then shaven in preparation for catheterization. An incision is made in the neck region and the right carotid artery cleared and isolated. A 2 French Millar Micro-tip Pressure Catheter (Millar Instruments, Houston, Tex.) is cannulated into the right carotid artery and threaded past the aorta and into the left ventricle. End diastolic pressure readings, max +/– dp/dt, systolic pressures and heart rate are determined continuously while compound or vehicle is infused. Measurements are recorded and analyzed using a PowerLab and the Chart 4 software program (ADInstruments, Mountain View, Calif.). Hemodynamics measurements are performed at a select infusion concentration. Blood samples are taken to determine the plasma concentration of the compounds.

Example 13

Left Coronary Artery Occlusion Model of Congestive Heart Failure

ANIMALS Male Sprague-Dawley CD (220-225 g; Charles River) rats are used in this experiment. Animals are allowed free access to water and commercial rodent diet under standard laboratory conditions. Room temperature is maintained at 20-23° C. and room illumination is on a 12/12-hour light/dark cycle. Animals are acclimatized to the laboratory environment 5 to 7 days prior to the study. The animals are fasted overnight prior to surgery.

OCCLUSION PROCEDURE Animals are anaesthetized with ketamine/xylazine (95 mg/kg and 5 mg/kg) and intubated with a 14-16-gauge modified intravenous catheter. Anesthesia level is checked by toe pinch. Core body temperature is maintained at 37° C. by using a heating blanket. The surgical area is clipped and scrubbed. The animal is placed in right lateral recumbency and initially placed on a ventilator with a peak inspiratory pressure of 10-15 cm $H_2O$ and respiratory rate 60-110 breaths/min. 100% $O_2$ is delivered to the animals by the ventilator. The surgical site is scrubbed with surgical scrub and alcohol. An incision is made over the rib cage at the $4^{th}$-$5^{th}$ intercostal space. The underlying muscles are dissected with care to avoid the lateral thoracic vein, to expose the intercostal muscles. The chest cavity is entered through $4^{th}$-$5^{th}$ intercostal space, and the incision expanded to allow visualization of the heart. The pericardium is opened to expose the heart. A 6-0 silk suture with a taper needle is passed around the left coronary artery near its origin, which lies in contact with the left margin of the pulmonary cone, at about 1 mm from the insertion of the left auricular appendage. The left coronary artery is occluded by tying the suture around the artery ("LCO"). Sham animals are treated the same, except that the suture is not tied. The incision is closed in three layers. The rat is ventilated until able to ventilate on its own. The rats are extubated and allowed to recover on a heating pad. Animals receive buprenorphine (0.01-0.05 mg/kg SQ) for post operative analgesia. Once awake, they are returned to their cage. Animals are monitored daily for signs of infection or distress. Infected or moribund animals are euthanized. Animals are weighed once a week.

EFFICACY ANALYSIS Approximately eight weeks after infarction surgery, rats are scanned for signs of myocardial infarction using echocardiography. Only those animals with decreased fractional shortening compared to sham rats are utilized further in efficacy experiments. In all experiments, there are four groups, sham+vehicle, sham+compound, LCL+vehicle and LCL+compound. At 10-12 weeks post LCL, rats are infused at a select infusion concentration. As before, five pre-dose M-Mode images are taken at 30 second intervals prior to infusion of compounds and M-mode images are taken at 30 second intervals up to 10 minutes and every minute or at five minute intervals thereafter. Fractional shortening is determined from the M-mode images. Comparisons between the pre-dose fractional shortening and compound treatment are performed by ANOVA and a post-hoc Student—Newman—Keuls. Animals are allowed to recover and within 7-10 days, animals are again infused with compounds using the hemodynamic protocol to determine hemodynamic changes of the compounds in heart failure animals. At the end to the infusion, rats are killed and the heart weights determined.

When tested as described above, compounds of Formula I are shown to have the desired activity.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:

1. A compound represented by Formula I:

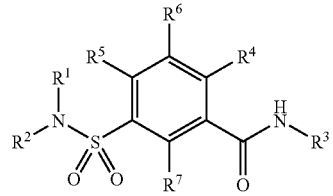

Formula I wherein:

$R^1$, $R^2$ and the nitrogen to which they are attached form a piperazin-1-yl ring, wherein the piperazin-1-yl ring is optionally substituted with one, two or three of the following groups: alkyl, halogen, hydroxy, alkoxy, alkylenedioxy, carboxy, acyloxy, alkoxycarbonyl, aminocarbonyl, cyano, acyl, oxo, nitro, amino, sulfanyl, sulfinyl, sulfonyl, aminosulfonyl, amidino, phenyl, benzyl, heteroaryl, heterocyclyl, aryloxy, aralikoxy, heteroaryloxy, and heteroaralkoxy;

$R^3$ is a phenyl, isoxazolyl, oxazolyl, pyridinyl, pyrazinyl, pyrimidinyl, tetrazol-5-yl, thiazolyl, thiadiazolyl or imidazolyl group, which is optionally substituted with a halogen, lower alkoxy, aryl or heteroaryl group;

$R^4$ is halogen;

$R^5$ is hydrogen, halogen, hydroxy, or lower alkyl; and $R^6$ and $R^7$ are independently selected from hydrogen, halogen, hydroxy, and lower alkyl;

or a pharmaceutically acceptable salt thereof.

2. The compound of claim 1 or a pharmaceutically acceptable salt thereof, wherein $R^3$ is an [1,3,4]thiadiazol-2-yl group which is optionally substituted with a phenyl group.

3. The compound of claim 1, or a pharmaceutically acceptable salt thereof, wherein $R^3$ is 5-phenyl-[1,3,4]thiadiazol-2-yl.

4. The compound of claim 2, or a pharmaceutically acceptable salt thereof, wherein $R^4$ is chloro; and $R^5$, $R^6$ and $R^7$ are hydrogen.

5. The compound of claim 1, or a pharmaceutically acceptable salt thereof, wherein $R^3$ is a 1H-imidazol-2-yl group.

6. The compound of claim 5, or a pharmaceutically acceptable salt thereof, wherein $R^4$ is chloro; and $R^5$, $R^6$ and $R^7$ are hydrogen.

7. The compound of claim 1, or a pharmaceutically acceptable salt thereof, wherein $R^3$ is oxazol-2-yl.

8. The compound of claim 7, or a pharmaceutically acceptable salt thereof, wherein $R^4$ is chloro; and $R^5$, $R^6$ and $R^7$ are hydrogen.

9. The compound of claim 1, or a pharmaceutically acceptable salt thereof, wherein $R^4$ is chloro; and $R^5$, $R^6$ and $R^7$ are hydrogen.

10. A pharmaceutical formulation comprising a pharmaceutically accepted excipient and a therapeutically effective amount of a compound of claim 1, or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 7,595,322 B2 | Page 1 of 1 |
| APPLICATION NO. | : 10/550398 | |
| DATED | : September 29, 2009 | |
| INVENTOR(S) | : Morgan et al. | |

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 358 days Delete the phrase "by 358 days" and insert -- by 679 days --

Signed and Sealed this

Tenth Day of August, 2010

David J. Kappos
*Director of the United States Patent and Trademark Office*